United States Patent
Hauser et al.

(10) Patent No.: US 10,449,257 B2
(45) Date of Patent: *Oct. 22, 2019

(54) SELF-ASSEMBLED COMPOSITE ULTRASMALL PEPTIDE-POLYMER HYDROGELS

(71) Applicant: Agency for Science, Technology and Research, Singapore (SG)

(72) Inventors: Charlotte Hauser, Singapore (SG); Yihua Loo, Singapore (SG); Andrew C. A. Wan, Singapore (SG); Michael Reithofer, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 209 days.

This patent is subject to a terminal disclaimer.

(21) Appl. No.: 14/356,116

(22) PCT Filed: Nov. 5, 2012

(86) PCT No.: PCT/SG2012/000421
§ 371 (c)(1),
(2) Date: May 2, 2014

(87) PCT Pub. No.: WO2013/066274
PCT Pub. Date: May 10, 2013

(65) Prior Publication Data
US 2014/0349933 A1    Nov. 27, 2014

(30) Foreign Application Priority Data
Nov. 4, 2011  (SG) ................. 201108178-3

(51) Int. Cl.
*A61K 47/36* (2006.01)
*A61K 31/7088* (2006.01)
(Continued)

(52) U.S. Cl.
CPC .......... *A61K 47/36* (2013.01); *A61K 31/7088* (2013.01); *A61K 35/28* (2013.01); *A61K 35/51* (2013.01); *A61K 35/545* (2013.01); *A61K 38/06* (2013.01); *A61K 38/07* (2013.01); *A61K 38/08* (2013.01); *A61K 38/18* (2013.01); *A61K 38/1825* (2013.01); *A61K 38/19* (2013.01); *A61K 47/183* (2013.01); *A61L 26/008* (2013.01); *A61L 26/0052* (2013.01); *A61L 26/0066* (2013.01); *A61L 26/0095* (2013.01); *A61L 27/26* (2013.01); *A61L 27/3834* (2013.01); *A61L 27/48* (2013.01); *A61L 27/52* (2013.01); *A61L 27/54* (2013.01); *C08L 5/00* (2013.01); *C08L 5/04* (2013.01); *C08L 5/08* (2013.01); *C08L 5/10* (2013.01); *C08L 5/16* (2013.01); *C08L 71/02* (2013.01); *C08L 89/00* (2013.01); *C12N 5/0068* (2013.01); *C12N 15/113* (2013.01); *C12N 2310/11* (2013.01); *C12N 2320/32* (2013.01); *C12N 2533/30* (2013.01); *C12N 2533/50* (2013.01); *C12N 2533/72* (2013.01)

(58) Field of Classification Search
CPC .... A61K 47/36; A61K 31/7088; A61K 35/28; A61K 35/51; A61K 35/545; A61K 38/06; A61K 38/07; A61K 38/08; A61K 38/18; A61K 38/1825; A61K 38/19; A61K 47/183; A61K 47/48215; A61L 26/0052; A61L 26/0066; A61L 26/008; A61L 26/0095; A61L 27/26; A61L 27/3834; A61L 27/48; A61L 27/52; A61L 27/54; C08L 5/00; C08L 5/04; C08L 5/08; C08L 5/10; C08L 5/16; C08L 71/02; C08L 89/00; C12N 5/0068; C14N 15/113
See application file for complete search history.

(56) References Cited

U.S. PATENT DOCUMENTS

2011/0081398 A1    4/2011    Sargeant et al.

FOREIGN PATENT DOCUMENTS

JP    2011-074075 A    4/2011
JP    2013-527833 A    7/2013
(Continued)

OTHER PUBLICATIONS

Xu et al., Twisted Nanotubes Formed from Ultrashort Amphiphilic Peptide I3K and Their Templating for the Fabrication of Silica Nanotubes, Chem. Mater. 2010, 22, 5165-5173.*
(Continued)

*Primary Examiner* — Karlheinz R. Skowronek
*Assistant Examiner* — Joseph Fischer
(74) *Attorney, Agent, or Firm* — Wolf, Greenfield & Sacks, P.C.

(57) ABSTRACT

The present invention relates to composite hydrogels comprising at least one non-peptidic polymer and at least one peptide having the general formula: $Z—(X)_m—(Y)_n—Z'_p$, wherein Z is an N-terminal protecting group; X is, at each occurrence, independently selected from an aliphatic amino acid, an aliphatic amino acid derivative and a glycine; Y is, at each occurrence, independently selected from a polar amino acid and a polar amino acid derivative; Z' is a C-terminal protecting group; m is an integer selected from 2 to 6; n is selected from 1 or 2; and p is selected from 0 or 1. The present invention further relates to methods of producing the composite hydrogels, to uses of the composite hydrogels for the delivery of drugs and other bioactive agents/moieties, as an implant or injectable agent that facilitates tissue regeneration, and as a topical agent for wound healing. The present invention further relates to devices and pharmaceutical or cosmetic compositions comprising the composite hydrogels and to medical uses of the composite hydrogels.

21 Claims, 23 Drawing Sheets
Specification includes a Sequence Listing.

(51) Int. Cl.

| | |
|---|---|
| A61K 35/28 | (2015.01) |
| A61K 35/51 | (2015.01) |
| A61K 35/545 | (2015.01) |
| A61K 38/06 | (2006.01) |
| A61K 38/07 | (2006.01) |
| A61K 38/08 | (2019.01) |
| A61K 38/18 | (2006.01) |
| A61K 38/19 | (2006.01) |
| A61K 47/18 | (2017.01) |
| A61L 26/00 | (2006.01) |
| A61L 27/26 | (2006.01) |
| A61L 27/38 | (2006.01) |
| A61L 27/48 | (2006.01) |
| A61L 27/52 | (2006.01) |
| A61L 27/54 | (2006.01) |
| C08L 5/00 | (2006.01) |
| C08L 5/04 | (2006.01) |
| C08L 5/08 | (2006.01) |
| C08L 5/10 | (2006.01) |
| C08L 5/16 | (2006.01) |
| C08L 71/02 | (2006.01) |
| C08L 89/00 | (2006.01) |
| C12N 5/00 | (2006.01) |
| C12N 15/113 | (2010.01) |

(56) References Cited

FOREIGN PATENT DOCUMENTS

| WO | WO2009/124388 | * 10/2009 | ............ C08L 101/14 |
| WO | WO 2011/123061 | * 10/2011 | ............... C07K 7/06 |
| WO | WO 2013/066274 A1 | 5/2013 | |

OTHER PUBLICATIONS

J. Zhu, Bioactive Modification of Poly(ethylene glycol) Hydrogels for Tissue Engineering, Biomater. Jun. 2010; 31(17):4639-4656 (equivalent to supplied Author Manuscript pp. 1-42).*

Kar et al., Organogel-Hydrogel Transformation by Simple Removal or Inclusion of N-Boc-Protection, Chem. Eur. J. 2011, 17, 14952-14961.*

Yang et al., Designer self-assembling peptide nanomaterials, Nano Today (2009) 4, 193-210.*

Wei et al., Dual-drug delivery system based on hydrogel/micelle composites, Biomaterials 30 (2009) 2606-2613.*

Zhao et al., Molecular self-assembly and applications of designer peptide amphiphiles, Chem. Soc. Rev. 2010, 39, 3480-3498.*

Um et al., Enzyme-catalyzed assembly of DNA hydrogel, Nature Materials, vol. 5, Oct. 2006, pp. 797-801.*

Genscript Nov. 3, 2009 webpage, one page screen shot (from www.waybackmachine.org).*

Sigma-Aldrich Amino Acids Reference Chart, 3 pages, downloaded 2014.*

Choi et al., Soft Matter, 2008, 4, 2383-2387.*

Hoare and Kohane, .Polymer 49 (2008) 1993-2007.*

Yang et al., Nano Today, 2009, 4, 193-210 (Year: 2009).*

International Search Report and Written Opinion for PCT/SG2012/000421 dated Dec. 17, 2012.

International Preliminary Report on Patentability for PCT/SG2012/000421 dated May 15, 2014.

Mishra et al., Ultrasmall natural peptides self-assemble to strong temperature-resistant helical fibers in scaffolds suitable for tissue engineering. Nano Today. 2011;6(3):232-9.

Japanese Notice of Reasons for Rejections for Japanese Application No. 2014-539909 dated Sep. 20, 2016.

* cited by examiner

SEQUENCE LISTING

```
<160> NUMBER OF SEQ ID NOS: 76

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 1

Leu Ile Val Ala Gly Asp Asp
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 2

Leu Ile Val Ala Gly Asp Glu
1               5
```

```
<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 3

Leu Ile Val Ala Gly Glu Asp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 4

Leu Ile Val Ala Gly Glu Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 5

Leu Ile Val Ala Gly Lys Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)
```

```
<400> SEQUENCE: 6

Leu Ile Val Ala Gly Ser Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 7

Ala Ile Val Ala Gly Lys Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 8

Ala Ile Val Ala Gly Ser Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 9

Leu Ile Val Ala Gly Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
```

```
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 10

Leu Ile Val Ala Gly Asp
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 11

Ile Leu Val Ala Gly Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 12

Leu Ile Val Ala Ala Asp
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 13

Leu Ala Val Ala Gly Asp
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 14

Ala Ile Val Ala Gly Asp
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 15

Leu Ile Val Ala Gly Glu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 16

Leu Ile Val Ala Gly Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 17

Leu Ile Val Ala Gly Ser
1               5
```

```
<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 18

Ile Leu Val Ala Gly Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 19

Ala Ile Val Ala Gly Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 20

Leu Ile Val Ala Gly Thr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)
```

```
<400> SEQUENCE: 21

Ala Ile Val Ala Gly Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (5)..(5)
<223> OTHER INFORMATION: BLOCKED (Optional C-terminal protecting group)

<400> SEQUENCE: 22

Leu Ile Val Ala Asp
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (5)..(5)
<223> OTHER INFORMATION: BLOCKED (Optional C-terminal protecting group)

<400> SEQUENCE: 23

Leu Ile Val Gly Asp
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (4)..(4)
<223> OTHER INFORMATION: BLOCKED (Optional C-terminal protecting group)

<400> SEQUENCE: 24

Ile Val Ala Asp
1

<210> SEQ ID NO 25
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
```

```
<220> FEATURE:
<221> NAME/KEY: misc_feature
<222> LOCATION: (4)..(4)
<223> OTHER INFORMATION: BLOCKED (Optional C-terminal protecting group)

<400> SEQUENCE: 25

Ile Ile Ile Asp
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (4)..(4)
<223> OTHER INFORMATION: BLOCKED (Optional C-terminal protecting group)

<400> SEQUENCE: 26

Ile Ile Ile Lys
1

<210> SEQ ID NO 27
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 27

Ile Val Asp
1

<210> SEQ ID NO 28
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 28

Ile Ile Asp
1

<210> SEQ ID NO 29
<211> LENGTH: 3
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 29

Leu Val Glu
1

<210> SEQ ID NO 30
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 30

Ile Val Glu
1

<210> SEQ ID NO 31
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 31

Leu Val Asp
1

<210> SEQ ID NO 32
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 32

Val Ile Glu
1
```

-continued

```
<210> SEQ ID NO 33
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 33

Val Ile Asp
1

<210> SEQ ID NO 34
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 34

Val Leu Asp
1

<210> SEQ ID NO 35
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 35

Val Leu Glu
1

<210> SEQ ID NO 36
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)
```

```
<400> SEQUENCE: 36

Leu Leu Glu
1

<210> SEQ ID NO 37
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 37

Leu Leu Asp
1

<210> SEQ ID NO 38
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 38

Ile Ile Glu
1

<210> SEQ ID NO 39
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 39

Ile Val Lys
1

<210> SEQ ID NO 40
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
```

```
<220> FEATURE:
<221> NAME/KEY: misc_feature
<222> LOCATION: (3)..(3)
<223> OTHER INFORMATION: Xaa is Orn
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 40

Ile Val Xaa
1

<210> SEQ ID NO 41
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: Xaa is Dbu
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 41

Ile Val Xaa
1

<210> SEQ ID NO 42
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: Xaa is Dpr
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 42

Ile Val Xaa
1

<210> SEQ ID NO 43
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)
```

```
<400> SEQUENCE: 43

Ile Val Ser
1

<210> SEQ ID NO 44
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 44

Leu Val Ser
1

<210> SEQ ID NO 45
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 45

Leu Val Lys
1

<210> SEQ ID NO 46
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: Xaa is Orn
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 46

Leu Val Xaa
1

<210> SEQ ID NO 47
<211> LENGTH: 3
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: Xaa is Dbu
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 47

Leu Val Xaa
1

<210> SEQ ID NO 48
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (3)..(3)
<223> OTHER INFORMATION: Xaa is Dpr
<220> FEATURE:
<221> NAME/KEY: misc_feature
<222> LOCATION: (3)..(3)
<223> OTHER INFORMATION: BLOCKED (Optional C-terminal protecting group)

<400> SEQUENCE: 48

Leu Val Xaa
1

<210> SEQ ID NO 49
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 49

Ile Leu Val Ala Gly Lys
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Orn
```

```
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 50

Ile Leu Val Ala Gly Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Dbu
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 51

Ile Leu Val Ala Gly Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Dpr
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 52

Ile Leu Val Ala Gly Xaa
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)
```

<400> SEQUENCE: 53

Ile Leu Val Ala Gly Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (7)..(7)
<223> OTHER INFORMATION: BLOCKED (Optional C-terminal protecting group)

<400> SEQUENCE: 54

Ile Leu Val Ala Gly Lys Cys
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 55

Ala Ile Val Ala Gly Lys
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Orn
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 56

Ala Ile Val Ala Gly Xaa
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Peptide

```
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Dbu
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 57

Ala Ile Val Ala Gly Xaa
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Dpr
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 58

Ala Ile Val Ala Gly Xaa
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Orn
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 59

Leu Ile Val Ala Gly Xaa
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
```

```
<220> FEATURE:
<221> NAME/KEY: misc_feature
<222> LOCATION: (6)..(6)
<223> OTHER INFORMATION: Xaa is Dbu
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 60

Leu Ile Val Ala Gly Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (6)..(6)
<223> OTHER INFORMATION: Xaa is Dpr
<220> FEATURE:
<221> NAME/KEY: misc_feature
<222> LOCATION: (6)..(6)
<223> OTHER INFORMATION: BLOCKED (Optional C-terminal protecting group)

<400> SEQUENCE: 61

Leu Ile Val Ala Gly Xaa
1               5

<210> SEQ ID NO 62
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (4)..(4)
<223> OTHER INFORMATION: Xaa is Orn
<220> FEATURE:
<221> NAME/KEY: misc_feature
<222> LOCATION: (4)..(4)
<223> OTHER INFORMATION: BLOCKED (Optional C-terminal protecting group)

<400> SEQUENCE: 62

Ile Ile Ile Xaa
1

<210> SEQ ID NO 63
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (4)..(4)
<223> OTHER INFORMATION: Xaa is Dbu
```

```
<220> FEATURE:
<221> NAME/KEY: misc_feature
<222> LOCATION: (4)..(4)
<223> OTHER INFORMATION: BLOCKED (Optional C-terminal protecting group)

<400> SEQUENCE: 63

Ile Ile Ile Xaa
1

<210> SEQ ID NO 64
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: BLOCKED (N-terminal protecting group)
<220> FEATURE:
<221> NAME/KEY: misc_feature
<222> LOCATION: (4)..(4)
<223> OTHER INFORMATION: Xaa is Dpr
<220> FEATURE:
<221> NAME/KEY: misc_feature
<222> LOCATION: (4)..(4)
<223> OTHER INFORMATION: BLOCKED (Optional C-terminal protecting group)

<400> SEQUENCE: 64

Ile Ile Ile Xaa
1

<210> SEQ ID NO 65
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 65

Leu Ile Val Ala Gly Asp
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 66

Leu Ile Val Ala Gly Lys
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MOD_RES
<222> LOCATION: (1)..(1)
<223> OTHER INFORMATION: ACETYLATION

<400> SEQUENCE: 67

Leu Ile Val Ala Gly Ser
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 68

Leu Ile Val Ala Gly Thr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 69

Ala Ile Val Ala Gly Ser
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 70

Ala Ile Val Ala Gly Lys
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 71

Ile Leu Val Ala Gly Lys
1               5
```

```
<210> SEQ ID NO 72
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 72

Ile Val Asp
1

<210> SEQ ID NO 73
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 73

Ile Val Lys
1

<210> SEQ ID NO 74
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 74

Leu Val Lys
1

<210> SEQ ID NO 75
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 75

Ala Val Lys
1

<210> SEQ ID NO 76
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
```

```
<400> SEQUENCE: 76

Ala Ile Val Ala Gly Asp
1               5
```

SELF-ASSEMBLED COMPOSITE ULTRASMALL PEPTIDE-POLYMER HYDROGELS

RELATED APPLICATIONS

This application is a U.S. National Stage application under 35 U.S.C. § 371 based on International Application No. PCT/SG2012/000421, filed Nov. 5, 2012, which claims priority in Singapore Patent Application No. SG 201108178-3, filed Nov. 4, 2011, the entire contents of each of which are incorporated by reference herein.

The present invention relates to composite hydrogels comprising at least one non-peptidic polymer and at least one peptide having the general formula: Z—$(X)_m$—$(Y)_n$—$Z'_p$, wherein Z is an N-terminal protecting group; X is, at each occurrence, independently selected from an aliphatic amino acid, an aliphatic amino acid derivative and a glycine; Y is, at each occurrence, independently selected from a polar amino acid and a polar amino acid derivative; Z' is a C-terminal protecting group; m is an integer selected from 2 to 6; n is selected from 1 or 2; and p is selected from 0 or 1. The present invention further relates to methods of producing the composite hydrogels, to uses of the composite hydrogels for the delivery of drugs and other bioactive agents/moieties, as an implant or injectable agent that facilitates tissue regeneration, and as a topical agent for wound healing. The present invention further relates to devices and pharmaceutical or cosmetic compositions comprising the composite hydrogels and to medical uses of the composite hydrogels.

BACKGROUND OF THE INVENTION

There is an unmet need for well-characterized, well-defined three-dimensional scaffolds for regenerative medicine. Progress in using stem cells for cell therapy is hampered by the need for feeder layers or coatings, such as Matrigel™ coatings. These coatings offer basically only two-dimensional (2D) support. An ideal synthetic cell culture substrate should maintain high proliferative rates while preserving the sternness of embryonic and induced pluripotent stem cells. There is also a need for scaffolds that reliably differentiate stem cells into specific lineages.

Furthermore, there is also a clinical need for similar bioactive scaffolds that can be implanted in vivo to regenerate tissue defects in orthopaedics and cosmetic surgery. Ideally, such constructs should be mechanically rigid to provide interim support and protect the cells from damage during recovery. The incorporation of bioactive therapeutics can facilitate integration with native tissue and prevent graft rejection. Biodegradation of the scaffold into biocompatible by-products as the tissue regenerates will further increase the attractiveness of the construct as an implant.

Degenerative disc disease affects 85% of people over age of 50, wherein current therapy involves surgical intervention to remove degenerated disc and fuse vertebrae or artificial disc implants. Surgery always has the risk of fatalities.

It would also be desirable that the scaffolds can be applied externally as dressings for various types of wounds, wherein incorporation of bioactive agents/moieties, such as bioadhesives, analgesics, anti-inflammatories and antibiotics would enhance wound healing and tissue regeneration.

An object of the invention is, thus, to ameliorate at least one of the above mentioned problems.

There is a need in the art for improved means and methods for scaffolds for regenerative medicine, including, for example, culturing cells, implants and drug delivery.

SUMMARY OF THE INVENTION

According to the present invention this object is solved by a composite hydrogel comprising at least one non-peptidic polymer and at least one peptide having the general formula: Z—$(X)_n$—$(Y)_n$—$Z'_p$, wherein
Z is an N-terminal protecting group;
X is, at each occurrence, independently selected from an aliphatic amino acid, an aliphatic amino acid derivative and a glycine;
Y is, at each occurrence, independently selected from a polar amino acid and a polar amino acid derivative;
Z' is a C-terminal protecting group;
m is an integer selected from 2 to 6;
n is selected from 1 or 2; and
p is selected from 0 or 1.

According to the present invention this object is solved by a method of producing a composite hydrogel according to the invention comprising the step of:
preparing an aqueous solution of a mixture of said at least one non-peptidic polymer and said at least one peptide; or
treating a preformed hydrogel comprising said at least one peptide with a solution of said at least one non-peptidic polymer.

According to the present invention this object is solved by the use of a composite hydrogel according to the invention as a 3-D scaffold for culturing cells.

According to the present invention this object is solved by the use of a composite hydrogel according to the invention as a device for drug delivery, preferably for sustained or controlled release drug delivery, or as an implant or as an injectable agent that gels in situ.

According to the present invention this object is solved by a 3-D scaffold for culturing cells comprising a composite hydrogel according to the invention.

According to the present invention this object is solved by a device for drug delivery, preferably sustained or controlled release drug delivery, comprising a composite hydrogel according to the invention.

According to the present invention this object is solved by an implant or injectable agent comprising a composite hydrogel according to the invention.

According to the present invention this object is solved by a pharmaceutical or cosmetic composition comprising a composite hydrogel according to the invention.

According to the present invention this object is solved by a composite hydrogel according to the invention for use in medicine.

According to the present invention this object is solved by a composite hydrogel according to the invention for use in regenerative medicine or for use in tissue engineering and tissue regeneration.

According to the present invention this object is solved by a composite hydrogel according to the invention for use in the treatment of wounds or degenerative diseases of the skeletal system, e.g. degenerative disc disease, or urinary incontinence.

According to the present invention this object is solved by a composite hydrogel according to the invention for cosmetic use.

According to the present invention this object is solved by an electronic device comprising a composite hydrogel according to the invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Numbers of amino acids, nucleotides, components, moieties or other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "3 to 8 amino acids" should be interpreted to include not only the explicitly recited values of 3 and 8, but also include individual values and sub-ranges within the indicated range. Thus, included in this numerical range are individual values, such as 3, 4, 5, 6, 7, 8, and sub-ranges, such as from 3 to 6, from 3 to 7 etc. This same principle applies to ranges reciting only one numerical value. Furthermore, such an interpretation should apply regardless of the breadth of the range or the characteristics being described.

Ultrasmall Peptide Polymer Composite Hydrogels

As described above, the present invention provides composite hydrogels comprising at least one non-peptidic polymer and at least one peptide.

The at least one peptide has the general formula:

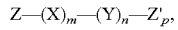

$Z-(X)_m-(Y)_n-Z'_p$, wherein

Z is an N-terminal protecting group;

X is, at each occurrence, independently selected from an aliphatic amino acid, an aliphatic amino acid derivative and a glycine;

Y is, at each occurrence, independently selected from a polar amino acid and a polar amino acid derivative;

Z' is a C-terminal protecting group;

m is an integer selected from 2 to 6;

n is selected from 1 or 2; and p is selected from 0 or 1.

The present invention provides a versatile composite hydrogel that combines self-assembling ultrasmall peptides and polymers to which bioactive therapeutics/agents (such as growth factors and prodrugs) can be added, such as by conjugation or encapsulation.

Preferably, the hydrophobicity decreases from the N-terminus to the C-terminus of said peptide of the composite hydrogel of the invention.

The composite hydrogels of the invention can comprise more than one peptide, such as two, three, four or more peptides, which can differ in their amino acid sequence, N- and/or C-terminal protecting group.

Preferably, said aliphatic amino acid and aliphatic amino acid derivative are selected from the group consisting of alanine (Ala, A), homoallylglycine, homopropargylglycine, isoleucine (Ile, I), norleucine, leucine (Leu, L) and valine (Val, V), said aliphatic amino acid is selected from the group consisting of alanine (Ala, A), isoleucine (Ile, I), leucine (Leu, L) and valine (Val, V).

Preferably, said polar amino acid and polar amino acid derivative are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, serine (Ser, S), homoserine, arginine (Arg, R), homoarginine, threonine (Thr, T), allo-threonine, lysine (Lys, K), hydroxylysine, N(6)-carboxymethyllysine, ornithine (Orn), 2,4-diaminobutyric acid (Dab or Dbu), 2,3-diaminopropionic acid (Dap or Dpr) and histidine (His, H), more preferably said polar amino acid and polar amino acid derivative are selected from the group consisting of aspartic acid (Asp, D), glutamic acid (Glu, E), cysteine (Cys, C), serine (Ser, S), threonine (Thr, T), lysine (Lys, K), ornithine (Orn), 2,4-diaminobutyric acid (Dab or Dbu) and 2,3-diaminopropionic acid (Dap or Dpr).

In one embodiment, said polar amino acid and polar amino acid derivative are selected from an acidic polar amino acid and an acidic polar amino acid derivative. Preferred acidic polar amino acids according to the present invention are aspartic acid (Asp, D) and glutamic acid (Glu, E).

In one embodiment, said polar amino acid and polar amino acid derivative are selected from a basic polar amino acid and a basic polar amino acid derivative. Preferred basic polar amino acids and basic polar amino acid derivatives according to the present invention are arginine (Arg, R), lysine (Lys, K), ornithine (Orn), 2,4-diaminobutyric acid (Dab or Dbu), 2,3-diaminopropionic acid (Dap or Dpr) and histidine (His, H).

Preferably, m is selected from 2 to 5.

Preferably, m+n is ≤7 or m+n is ≤6.

For example, m is 5 and n is 2; or m is 5 and n is 1; or m is 4 and n is 1; or m is 3 and n is 1; or m is 2 and n is 1.

For example, m+n is 3 or 4 or 5 or 6 or 7.

Preferably, said peptide is selected from the group consisting of Z-LIVAGDD-Z'$_p$ (SEQ ID NO: 1), Z-LIVAGDE-Z'$_p$ (SEQ ID NO: 2), Z-LIVAGED-Z'$_p$ (SEQ ID NO: 3), Z-LIVAGEE-Z'$_p$ (SEQ ID NO: 4), Z-LIVAGKC-Z'$_p$ (SEQ ID NO: 5), Z-LIVAGSC-Z'$_p$ (SEQ ID NO: 6), Z-AIVAGKC-Z'$_p$ (SEQ ID NO: 7), Z-AIVAGSC-Z'$_p$ (SEQ ID NO: 8), Z-LIVAGC-Z'$_p$ (SEQ ID NO: 9), Z-LIVAGD-Z'$_p$ (SEQ ID NO: 10), Z-ILVAGD-Z'$_p$ (SEQ ID NO: 11), Z-LIVAAD-Z'$_p$ (SEQ ID NO: 12), Z-LAVAGD-Z'$_p$ (SEQ ID NO: 13), Z-AIVAGD-Z'$_p$ (SEQ ID NO: 14), Z-LIVAGE-Z'$_p$ (SEQ ID NO: 15), Z-LIVAGK-Z'$_p$ (SEQ ID NO: 16), Z-LIVAGS-Z'$_p$ (SEQ ID NO: 17), Z-ILVAGS-Z'$_p$ (SEQ ID NO: 18), Z-AIVAGS-Z'$_p$ (SEQ ID NO: 19), Z-LIVAGT-Z'$_p$ (SEQ ID NO: 20), Z-AIVAGT-Z'$_p$ (SEQ ID NO: 21), Z-LIVAD-Z'$_p$ (SEQ ID NO: 22), Z-LIVGD-Z'$_p$ (SEQ ID NO: 23), Z-IVAD-Z'$_p$ (SEQ ID NO: 24), Z-IIID-Z'$_p$ (SEQ ID NO: 25), Z-IIIK-Z'$_p$ (SEQ ID NO: 26), Z-IVD-Z'$_p$ (SEQ ID NO: 27), Z-IID-Z'$_p$ (SEQ ID NO: 28), Z-LVE-Z'$_p$ (SEQ ID NO: 29), Z-IVE-Z'$_p$ (SEQ ID NO: 30), Z-LVD-Z'$_p$ (SEQ ID NO: 31), Z-VIE-Z'$_p$ (SEQ ID NO: 32), Z-VID-Z'$_p$ (SEQ ID NO: 33), Z-VLD-Z'$_p$ (SEQ ID NO: 34), Z-VLE-Z'$_p$ (SEQ ID NO: 35), Z-LLE-Z'$_p$ (SEQ ID NO: 36), Z-LLD-Z'$_p$ (SEQ ID NO: 37), Z-IIE-Z'$_p$ (SEQ ID NO: 38), Z-IVK-Z'$_p$ (SEQ ID NO: 39), Z-IV(Orn)-Z'$_p$ (SEQ ID NO: 40), Z-IV(Dab)-Z'$_p$ (SEQ ID NO: 41), Z-IV(Dap)-Z'$_p$ (SEQ ID NO: 42), Z-IVS-Z'$_p$ (SEQ ID NO: 43), Z-LVS-Z'$_p$ (SEQ ID NO: 44), Z-LVK-Z'$_p$ (SEQ ID NO: 45), Z-LV(Orn)-Z'$_p$ (SEQ ID NO: 46), Z-LV(Dab)-Z'$_p$ (SEQ ID NO: 47), Z-LV(Dap)-Z'$_p$ (SEQ ID NO: 48), Z-ILVAGK-Z'$_p$ (SEQ ID NO: 49), Z-ILVAG(Orn)-Z'$_p$ (SEQ ID NO: 50), Z-ILVAG(Dab)-Z'$_p$ (SEQ ID NO: 51), Z-ILVAG(Dap)-Z'$_p$ (SEQ ID NO: 52), Z-ILVAGS-Z'$_p$ (SEQ ID NO: 53), Z-ILVAGKC-Z'$_p$ (SEQ ID NO: 54), Z-AIVAGK-Z'$_p$ (SEQ ID NO: 55), Z-AIVAG(Orn)-Z'$_p$ (SEQ ID NO: 56), Z-AIVAG(Dab)-Z'$_p$ (SEQ ID NO: 57), Z-AIVAG(Dap)-Z'$_p$ (SEQ ID NO: 58), Z-LIVAG(Orn)-Z'$_p$ (SEQ ID NO: 59), Z-LIVAG(Dab)-Z'$_p$ (SEQ ID NO: 60), Z-LIVAG(Dap)-Z'$_p$ (SEQ ID NO: 61), Z-III(Orn)-Z'$_p$ (SEQ ID NO: 62), Z-III(Dab)-Z'$_p$ (SEQ ID NO: 63) and Z-III(Dap)-Z'$_p$ (SEQ ID NO: 64).

Exemplary peptides having an acetyl group as N-terminal protecting group and lacking a C-terminal protecting group are designated with SEQ ID NOs: 65 to 76.

The composite hydrogels of the invention can comprise more than one non-peptidic polymer, such as two, three, four or more non-peptidic polymers, such as a mixture of a linear and a branched polymer.

Preferably, said non-peptidic polymer is a hydrophilic or amphiphilic polymer.

Preferably, said non-peptidic polymer is a linear or branched polymer.

In one embodiment, said branched polymer is a dendrimer. Exemplary dendrimers are poly(amido amine) dendrimers, dendrons, polylysine dendrimers and polypropylenimine dendrimers.

In one embodiment, said non-peptidic polymer is a cationic polymer or an anionic polymer or a neutral polymer or a combination of any of the foregoing.

Preferably, the cationic polymer is selected from the group consisting of chitosan, chitin, poly(amido amine) dendrimers, polyphosphoamidate, polyethyleneimine, spermine, spermidine, putrescine and polyomithine. In a particular preferred embodiment, the cationic polymer is chitosan.

Preferably, the anionic polymer is selected from the group consisting of alginate, heparin sulfate, anionic dendrimers, polycarbonates, polysulfonates, chrondroitin sulfate, chrondroitin sulfate proteoglycan, dextran sulfate, dermatan sulfate, keratin sulfate, sulfated polysaccharides, sialoproteins, fucoidan, asialofetuin, asialomucin and nucleic acids, e.g. RNA and DNA.

Preferably, the neutral polymer is selected from the group consisting of polyethylene glycol (PEG), dextrans, cyclodextrins, polyvinylalcohols, poly(vinyl pyrrolidone), polysaccharides, polyesters, neutral dendrimers, polyoxyethylene, polyacrylamide, polymethacrylates, poly(phosphoric acid), poly(silicic acid), polyphosphazenes and polyurethanes. Preferably, the neutral polymer is linear or branched PEG.

In one embodiment, said non-peptidic polymer is a cationic polymer, and said polar amino acid and polar amino acid derivative are selected from an acidic polar amino acid and an acidic polar amino acid derivative.

In another embodiment, said non-peptidic polymer is an anionic polymer, e.g. a nucleic acid or an oligo- or polynucleotide, and said polar amino acid and polar amino acid derivative are selected from a basic polar amino acid and a basic polar amino acid derivative.

In yet another embodiment, said non-peptidic polymer is a neutral polymer, and said polar amino acid and polar amino acid derivative are selected from a neutral polar amino acid and a neutral polar amino acid derivative (i.e. a polar amino acid or polar amino acid derivative with no electrical charge).

In yet another embodiment, said non-peptidic polymer is a neutral polymer, and said polar amino acid and polar amino acid derivative are selected from an acidic polar amino acid and an acidic polar amino acid derivative.

In yet another embodiment, said non-peptidic polymer is a neutral polymer, and said polar amino acid and polar amino acid derivative are selected from a basic polar amino acid and a basic polar amino acid derivative.

In one embodiment, said non-peptidic polymer is a biocompatible polymer.

In one embodiment, the composite hydrogel further, comprises at least one bioactive agent.

The composite hydrogels of the invention can comprise more than one bioactive agent, such as two, three, four or more bioactive agents.

Preferably, said at least one bioactive agent is selected from the group consisting of
nucleic acids,
(poly)peptides,
virus particles,
oligosaccharides,
polysaccharides,
vitamins,
sialic acids,
antigens,
antibiotics,
anti-inflammatory molecules,
vaccines,
drugs,
prodrugs,
nanoparticles
and other organic or inorganic compounds.

In one embodiment, said at least one bioactive agent is a growth factor or a nucleic acid encoding a growth factor.

For example, the growth factor comprises a cytokine, or the nucleic acid encodes a cytokine.

In one embodiment, said at least one bioactive agent is a cell adhesion molecule or a nucleic acid encoding a cell adhesion molecule.

In one embodiment, said at least one bioactive agent is encapsulated by the composite hydrogel.

In one embodiment, said at least one bioactive agent is conjugated to the composite hydrogel.

In one embodiment, said at least one bioactive agent is coupled to at least one functional group present on the non-peptidic polymer.

In another embodiment, said at least one bioactive agent is coupled to at least one functional group present on said peptide.

Preferably, said at least one functional group is selected from the group consisting of amines, carboxylic acids, thiols, alcohols, carbohydrates, amides, imines, imides, azides, nitriles, peroxides, esters, thioesters, phosphates, aryls, aldehydes, ketones, sulfates, sulfites, nitrates, nitrites, phosphonates, silanes, alkanes, alkenes and alkynes.

In one embodiment, the at least one bioactive agent is a negatively charged bioactive agent, such as a nucleic acid, and the non-peptidic polymer is a cationic polymer.

In one embodiment, the at least one bioactive agent is a positively charged bioactive agent, and the non-peptidic polymer is an anionic polymer.

In one embodiment, the at least one bioactive agent is a neutral bioactive agent, and the non-peptidic polymer is a neutral polymer.

In one embodiment, the non-peptidic polymer is a heterocyclic polymer.

Preferably, the heterocyclic polymer is a nucleic acid or an oligo- or polynucleotide.

Preferably, the nucleic acid, oligonucleotide and/or polynucleotide comprises or is DNA, RNA, modified and artificial nucleic acids and nucleic acid analogues (such as PNA, LNA, GNA, TNA), or combinations thereof.

In one embodiment, said nucleic acid, oligo- or polynucleotide is selected from the group consisting of plasmid DNA, aptamers, mRNA, microRNA, siRNA and short hairpin RNA.

In one embodiment of the invention, said nucleic acid, oligo- or polynucleotide is a bioactive agent or encodes a bioactive agent. In one embodiment, the nucleic acid is the non-peptidic polymer of the composite hydrogel as well as the bioactive agent.

In one embodiment, said nucleic acid, oligo- or polynucleotide encodes a growth factor, such as a cytokine.

In one embodiment, said nucleic acid, oligo- or polynucleotide encodes a cell adhesion molecule.

In one embodiment, said nucleic acid, oligo- or polynucleotide encodes a secreted molecule, such as insulin.

In one embodiment, said nucleic acid, oligo- or polynucleotide encodes an intracellular molecule than can influence cell behavior.

In one embodiment, said nucleic acid, oligo- or polynucleotide encodes a membrane-bound molecule that is able to influence cell behavior.

In one embodiment of the invention, the nucleic acid is conjugated to a (further) bioactive agent as defined above. In this embodiment, the nucleic acid is the non-peptidic polymer of the composite hydrogel, which comprises another component as the bioactive agent.

Preferably, said N-terminal protecting group has the general formula —C(O)—R, wherein R is selected from the group consisting of H, alkyl and substituted alkyl, such as methyl, ethyl, propyl, isopropyl, butyl and isobutyl.

In one embodiment, said N-terminal protecting group is an acetyl group.

In one embodiment, the C-terminal protecting group is an amide group, wherein, preferably, the C-terminus of said at least one peptide has the formula —CONHR or —CONRR', with R and R' being selected from the group consisting of H, alkyl and substituted alkyl.

In one embodiment, the C-terminal protecting group is an ester group, wherein, preferably, the C-terminus has the formula —CO$_2$R, with R being selected from the group consisting of H, alkyl and substituted alkyl.

In one embodiment, said C-terminal protecting group is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate and nitrate.

Preferably, the at least one non-peptidic polymer is present at a concentration of 50% (w/w) or less, with respect to the total weight of said composite hydrogel.

Preferably, the at least one non-peptidic polymer is present at a concentration of 40% (w/w) or less, with respect to the total weight of said composite hydrogel.

Preferably, the total nucleic acid content of said composite hydrogel is 50% or less by charge ratio.

Methods of Producing the Composite Hydrogels

As described above, the present invention provides a method of producing a composite hydrogel of the invention. Said method comprises the step of:
preparing an aqueous solution of a mixture of said at least one non-peptidic polymer and said at least one peptide; or
treating a preformed hydrogel comprising said at least one peptide with a solution of said at least one non-peptidic polymer.

The method of the invention comprises the self-assembly of the peptide(s).

In the method of the invention,
more than one peptide,
such as two, three, four or more peptides,
and/or
more than one non-peptidic polymer,
such as two, three, four or more non-peptidic polymers,
such as a mixture of a linear and a branched (cationic) polymer,
can be utilized.

The method can further comprises at least one of the steps of:
adding at least one bioactive agent, e.g. at least one bioactive agent as defined above;
adding an ultraviolet (UV) photoinitiator to said aqueous solution and exposing said aqueous solution to UV irradiation;
adding at least one coupling reagent to facilitate the formation of covalent linkages (e.g. between the polymer and the peptide);
adding at least one compound (i.e. acidic, neutral, basic and/or charged compounds) acting as gelation enhancer;
adding at least one buffer, preferably at least one physiologically acceptable buffer.

Preferably, said at least one bioactive agent is added to the polymer before self-assembly of the composite hydrogel or to the composite hydrogel post-assembly.

Thereby, also more than one bioactive agent, such as two, three, four or more, can be utilized By modifying and choosing the reaction conditions, such as choice of components, concentration of the components, chemical structure of the components, the resulting composite hydrogel and its properties (such as mechanical strength, elasticity, release kinetics, shape) can be tuned according to the desired application, as discussed herein.

Uses of the Composite Hydrogels, 3D Scaffolds, Devices and Implants

As described above, the present invention provides the use of a composite hydrogel according to the invention as a 3-D scaffold for culturing cells.

Preferably, the cells are stem cells, including embryonic stem cells, human induced pluripotent stem (iPS) cells, progenitor cells and adult stem cells, cord blood stem cells, mesenchymal stem cells, adipose-derived stem cells, hematopoietic stem cells.

As described above, the present invention provides the use of a composite hydrogel according to the invention as a device for drug delivery, preferably for sustained or controlled release drug delivery, or as an implant or as an injectable agent that gels in situ. The injectable agent is prepared in a way that it gels in situ (i.e. the formation of the composite hydrogel occurs during or after the process of injection) by controlling/modifying the speed of gel formation.

As described above, the present invention provides a 3-D scaffold for culturing cells comprising a composite hydrogel according to the invention.

Preferably, the 3-D scaffold is for culturing stem cells, including embryonic stem cells, human induced pluripotent stem (iPS) cells, progenitor cells and adult stem cells, cord blood stem cells, mesenchymal stem cells, adipose-derived stem cells, hematopoietic stem cells.

As described above, the present invention provides a device for drug delivery, preferably sustained or controlled release drug delivery, comprising a composite hydrogel according to the invention.

For example, the device can be a delivery device for specific growth factors and nucleic acids, such as mRNA or DNA.

In one embodiment, the device further comprises electrical components.

As described above, the present invention provides an implant or injectable agent comprising a composite hydrogel according to the invention.

The implant can take on different forms, shapes and sizes, such as sol hydrogels, dried membranes and viscous gels. In addition, the hydrogels can be molded into different shapes such as sheets, discs, membranes, spheres and other three-dimensional structures.

As described above, the present invention provides a pharmaceutical or cosmetic composition comprising a composite hydrogel according to the invention.

The pharmaceutical or cosmetic composition(s) can comprise further components, such as excipient(s).

As described above, the present invention also provides an electronic device comprising a composite hydrogel according to the invention.

Medical and Cosmetic Uses of the Composite Hydrogels

As described above, the present invention provides the composite hydrogel according to the invention for use in medicine.

As described above, the present invention provides the composite hydrogel according to the invention for use in regenerative medicine or for use in tissue engineering and tissue regeneration. For example, the composite hydrogel according to the invention may be used for the regeneration of adipose and cartilage tissue.

Furthermore, the present invention provides the composite hydrogel according to the invention for use in the treatment of wounds or degenerative diseases of the skeletal system, e.g. degenerative disc disease, or urinary incontinence. The composite hydrogel according to the invention can be provided in the form of injectable dermal fillers and 3-D scaffolds.

As described above, the present invention provides the composite hydrogel according to the invention for cosmetic use, preferably cosmetic use by topical application.

DEFINITIONS

The term "composite hydrogel", as used herein, is meant to refer to a hydrogel (i.e. a water-containing, but water-insoluble gel) comprising a 3-dimensional network of a non-peptidic polymer and ultrasmall peptides as defined herein. The non-peptidic polymer interacts with the peptides electrostatically or via van der Waals interactions, hydrogen bonds or covalent bonds. Preferably, the at least one non-peptidic polymer and the at least one peptide are covalently crosslinked or conjugated.

The term "ultrasmall" peptides, as used herein, refers to peptides having amino acid sequences with 3 to 8 amino acids, preferably 3 to 7 amino acids, more preferably 3 to 6 amino acids. Preferably, the peptides utilized in the present invention are self-assembling peptides, i.e. they self-assemble into higher-order supramolecular structures, such as peptide fibrils (see also FIG. 1) which can serve as a fibrous scaffold or network. The peptides utilized in the present invention may also have cell-penetrating properties, wherein the bioactive agent(s) present in the composite hydrogel may further enhance this inherent peptide property. Furthermore, peptides utilized in the present invention may be stimuli-responsive peptides, i.e. responsive to light, pH and salt, wherein the non-peptidic polymer and/or bioactive agent(s) may amplify or confer this property.

The terms "amino acid" and "amino acid derivative", as used herein, are meant to include naturally and non-naturally occurring L- and D-amino acids and amino acid derivatives, peptidomimetic amino acids and non-standard amino acids that are not made by a standard cellular machinery or are only found in proteins after post-translational modification or as metabolic intermediates. For example, when reference is made to a particular amino acid, e.g. leucine (Leu, L), reference is made to both the L- and D-enantiomer of this particular amino acid, e.g. L- and D-leucine. A peptide according to the present invention may be exclusively composed of L-amino acids and/or amino acid derivatives or exclusively composed of D-amino acids and/or amino acid derivatives. Alternatively, the peptide may be composed of both L- and D-amino acids and/or amino acid derivatives.

The term "polymer" as used herein refers to any polymeric molecule with at least two repeating units, wherein molecules with only two repeating units, such as di(ethylene glycol)diacrylate (DEGDA), are explicitly included. The term also encompasses multimeric structures with repeating cationic/anionic/neutral building blocks, as well as biologically relevant polymers, such as oligonucleotides, polysaccharides, lipid-like polymers etc.

The term "anionic polymer", as used herein, is meant to refer to a polymer composed of negatively charged or negatively chargeable macromolecules.

The term "cationic polymer", as used herein, is meant to refer to a polymer composed of positively charged or positively chargeable macromolecules.

The term "neutral polymer", as used herein, is meant to refer to a polymer that has no electrical charge or ionisable groups.

The term "bioactive agent" or "bioactive moiety", as used herein, is meant to refer to agents (i.e. molecules or compounds) that interact with an animal body, an organ, a cell tissue, cells, cell compartments or specific molecules within any of the aforementioned entities, in particular therapeutic molecules. The term also includes diagnostic markers, such as fluorophores, dyes, inorganic and organic nanodots and quantum dots.

The term "growth factor", as used herein, is meant to refer to a synthetic or naturally occurring substance capable of stimulating cellular growth, proliferation and cellular differentiation. Growth factors typically act as signaling molecules between cells. Examples are cytokines and hormones that bind to specific receptors on the surface of their target cells. Particularly preferred examples include basic fibroblast growth factor (bFGF), vascular endothelial growth factor (VEGF), connective tissue growth factor (CTGF), transforming growth factor beta (TGF-beta), Platelet-derived growth factor (PDGF), epidermal growth factor (EGF), nerve growth factor (NGF), insulin-like growth factor (IGF), stem cell factor (SCF), macrophage migration inhibitory factor (MIF), sarcoma growth factor (SGF), bone morphogenetic proteins (BMPs), growth differentiation factors (GDFs), hepatocyte growth factor (HGF), macrophage slowing factor (MSF), hematopoietic growth factors, such as granulocyte colony stimulating factor (G-CSF) and granulocyte macrophage-colony stimulating factor (GM-CSF), melanoma inhibitory activity (MIA), growth hormone (GH), thrombopoietin (TPO), erythropoietin, insulin, prolactin, myostatin, leptin, neurotrophins, anti-inflammatory cytokines and interleukins.

The term "oligonucleotide", as used herein, is meant to refer to a short nucleic acid polymer, typically with fifty or fewer bases.

The term "polynucleotide", as used herein, is meant to refer to a nucleic acid polymer with 20 or more bases, preferably 50 or more bases, more preferably 100 or more bases.

The term "3-D scaffold for culturing cells", as used herein, is meant to refer to a 3-dimensional scaffold that allows for the embedding of cells and the proliferation and, preferably, differentiation of the embedded cells. The terms "scaffold", "matrix" and "substrate" can be used interchangeably.

The term "implant" as used herein, is meant to refer to a medical device manufactured to replace a missing biological structure, support a damaged biological structure, or enhance an existing biological structure.

The term "regenerative medicine" refers to the process of replacing or regenerating human cells, tissues or organs to restore or establish normal function. This field holds the promise of regenerating damaged tissues and organs in the body by replacing damaged tissue and/or by stimulating the body's own repair mechanisms to heal previously irreparable tissues or organs. Regenerative medicine also empowers scientists to grow tissues and organs in the laboratory and safely implant them when the body cannot heal itself. Importantly, regenerative medicine has the potential to solve the problem of the shortage of organs available for donation compared to the number of patients that require life-saving organ transplantation. Depending on the source of cells, it can potentially solve the problem of organ transplant rejection if the organ's cells are derived from the patient's own tissue or cells. Regenerative medicine also refers to a group of biomedical approaches to clinical therapies. Examples include the injection of stem cells or progenitor cells (cell therapies); the induction of regeneration by biologically active molecules administered alone or as a secretion by infused cells (immunomodulation therapy); and transplantation of in vitro grown cells, organs and tissues (tissue engineering).

The present invention discloses a versatile new biomaterial and a versatile new technology: the development of three-dimensional (3D) composite ultrasmall peptide-polymer hydrogels, in which the formulation can be modified and optimized to create niche cell culture substrates and tissue engineering scaffolds for clinical applications without the need for feeder cells. Ultrasmall peptides (i.e. (3 to 6 (or 7 or 8) amino acids long) self-assemble in water to supramolecular aggregates that further condense to three-dimensional fibrous meshes, entrapping up to 99.9% water. The incorporation of polymers that interact with the peptides electrostatically, or by van der Waals interaction, hydrogen bondings or covalent bonds enhances the mechanical properties, namely increases elasticity (resistance to strain), while maintaining the high mechanical stiffness of the hydrogels. The resulting composite hydrogels are stable in high salt conditions, heat resistant, and can be moulded to specific geometries during the gelation process. Furthermore, the presence of functional groups on the polymer facilitates the conjugation of bioactive therapeutics, such as growth factors and prodrugs. This offers another delivery strategy in addition to encapsulation. The release kinetics of the immobilized and encapsulated therapeutics can be modulated by various strategies, including peptide-polymer composition, concentration and degradation characteristics. In summary, this invention provides a versatile composite hydrogel that combines self-assembling ultrasmall peptides and polymers to which bioactive therapeutics (such as growth factors and prodrugs) can be added, such as by conjugation or encapsulation.

Advantages of the present inventions include at least the following:

The composite hydrogels of the invention combine the high mechanical stiffness of ultrasmall peptide hydrogels with the elastic properties of synthetic polymers.

The stability of peptide hydrogels improves with the addition of polymeric components. In particular, the composite hydrogels of the invention are significantly more stable in high salt environments.

Stimuli-responsive polymeric components enable crosslinking in specific environments to further increase hydrogel stability.

The formulation of the composite hydrogels of the invention is extremely versatile—the gelation, degradation/clearance and therapeutic release kinetics can be modulated by tailoring the polymer and peptide characteristics.

Bioactive therapeutics/agents, such as nucleic acids (DNA, RNA, plasmids, aptamers), oligonucleotides, viruses, proteins, peptides, such as growth factors, pro-drugs and other small compounds can be immobilized on the hydrogels of the invention.

The water content of the hydrogel can be increased significantly by incorporating highly hydrophilic polymers.

The composite hydrogels offer a package solution for patients on demand for therapies using tissue engineering, i.e. a package solution for patient-tailored cell therapy. The self, assembled composite ultrasmall peptide-polymer hydrogels of the invention offer an overall solution, starting from taking patient's healthy tissue, such as fibroblasts, and change it to the cell type where a therapy is needed.

The composite ultrasmall peptide-polymer hydrogels of the present invention have biomedical applications such as cell culture substrates for maintaining and differentiating stem cells, matrixes/scaffolds for drug delivery and regenerative medicine, and membranes in biomedical devices. They can also be applied as encapsulation matrices and membranes for inorganic materials in the development of electronic devices. The use of different functional groups provides additional opportunities to fine tune material properties. In addition, variation of the polymer to linear to branched structures and even 3-D structures enables the binding of different biologically important molecules and compounds. This includes nucleic acids (DNA, RNA, plasmids, aptamers), oligonucleotides, viruses, proteins, peptides, such as growth factors, pro-drugs and other small compounds, as well as inorganic compounds and organic compounds, such as fluorophores and dyes. Inorganic and organic nanodots and quantum dots can also be used.

The present invention including the novel biomaterial and its associated technology of use enables the development of:
1. cell culture substrates for stem cells, particularly through the immobilization of specific growth factors for maintaining their pluripotency or promoting differentiation into specific lineages;
2. injectable therapies for tissue engineering, particularly in orthopaedic and aesthetic surgery applications;
3. patient-tailored 'made-to-measure' tissue-engineered scaffolds that fit the size of the defect exactly;
4. biodegradable scaffolds for regenerative medicine to provide interim mechanical support during the recovery process;
5. tissue engineered constructs containing autologous stem cells or ex vivo differentiated cells for cell therapy, providing an ideal microenvironment to regenerate the damaged tissue at the implant site;
6. biocompatible delivery systems for controlled and sustained release of encapsulated or immobilized biotherapeutics (such as drug/gene/growth factor).

As discussed above, there is an unmet need for well-characterised, well-defined three dimensional scaffolds for regenerative medicine. Progress in using stem cells for cell therapy is hampered by the need for feeder layers or coatings, such as Matrigel™ coatings. These prior art coatings offer basically only 2-dimensional support. An ideal synthetic cell culture substrate should maintain high proliferative rates while preserving the sternness of embryonic and induced pluripotent stem cells. Furthermore, there is also a need for scaffolds that reliably differentiate stem cells into specific lineages. Similar bioactive scaffolds can be implanted in vivo to regenerate tissue defects in orthopaedics and cosmetic surgery.

As described herein, the present invention discloses composite ultrasmall peptide-polymer hydrogels, a novel biomaterial and an enabling versatile technology, which improve the means and methods of the prior art.

The technology of the present invention is set-up to form the basis of a low-cost, chemically well-defined and well-characterised substrate for the large-scale, feeder-free culture of stem cells, such as for pluripotent stem cells. Thereby, immobilized growth factors on the scaffold will maintain the sternness and proliferation of stem cells or drive their differentiation into specific lineages. The tuneable properties of the composite hydrogels will also enable convenient harvesting of cells, eliminating the use of enzymes. Sustained and controlled release of certain bioactive agents, such as growth factors and cytokines, into the extracellular milieu can be also achieved by encapsulation in the hydrogels.

The high mechanical strength and capacity for in situ gelation, renders the present technology attractive as implantable scaffolds that promote regeneration of native tissue following orthopaedic and aesthetic surgery. The rigidity of the constructs provides interim support and protects the cells from damage during recovery. The incorporation of bioactive therapeutics to facilitate integration with native tissue and prevent graft rejection will ensure successful clinical outcomes. Biodegradation of the scaffold into biocompatible by-products as the tissue regenerates further increases the attractiveness of the construct as an implant.

Sustained and controlled drug release devices can be developed using the composite hydrogel. The release kinetics of the immobilized and encapsulated therapeutics can be modulated by various strategies including peptide-polymer composition, concentration and degradation characteristics.

The composite hydrogels of the invention form when a mixture of ultrasmall peptides and polymers dispersed in aqueous solutions self-assemble into scaffolds that entrap large amounts of water. The schematic of ultrasmall peptide-polymer composite hydrogel formation is depicted in FIG. 1. It is hypothesized that the peptides initially self-assemble into peptide fibrils, which subsequently interact with the polymer, thereby strengthening the fibril network. The resulting macrostructures entrap water, particularly when the selected polymer is hydrophilic.

Other aspects and advantages of the invention will become apparent to those skilled in the art from a review of the ensuing description.

The following examples and drawings illustrate the present invention without, however, limiting the same thereto.

Composite hydrogels are formed by mixing self-assembling ultrashort peptides with linear and branched polymers. The polymeric component can be incorporated into the mixture during the peptide self-assembling process or post-assembly. The polymeric component can interact with the peptides electrostatically, or by van der Waals interaction, hydrogen bondings or covalent bonding, thereby forming cross-links between peptide fibers, and/or providing avenues for the attachment for bioactive moieties of interest.

Figure 2:
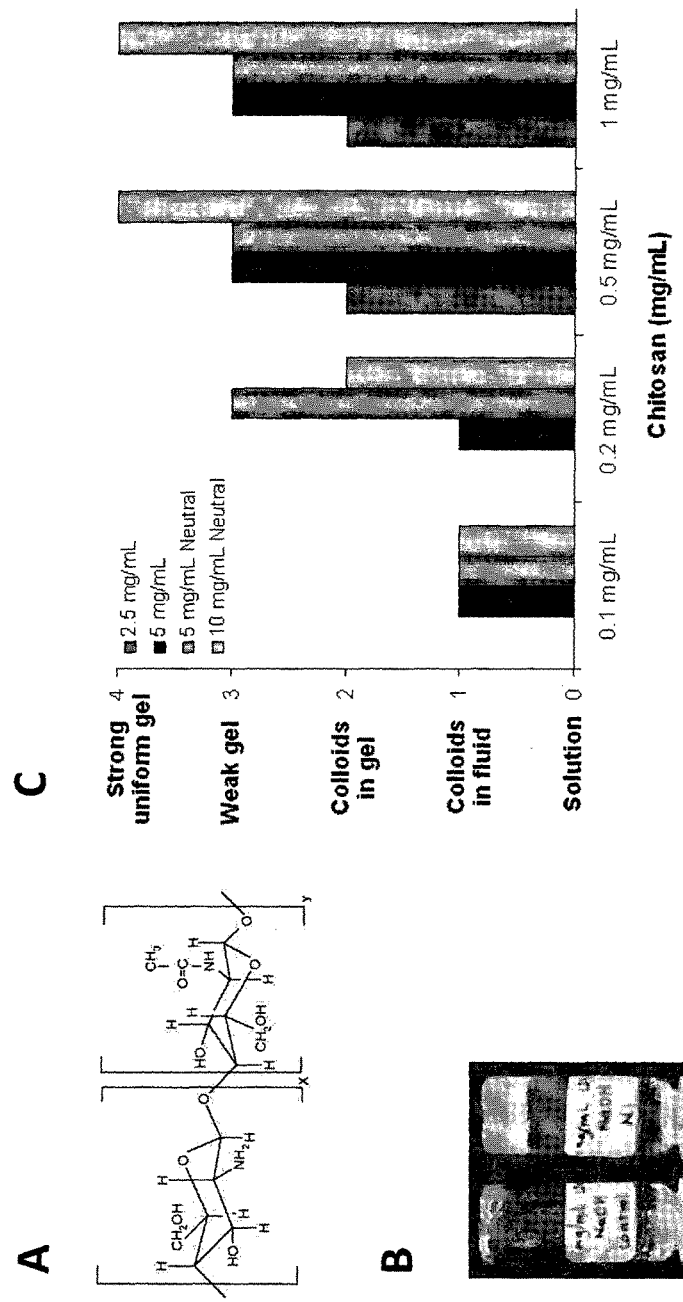

FIG. 2. Ultrashort peptide-cationic polymer composite hydrogels

Ultrashort peptides with acidic polar head groups form stable composite hydrogels when mixed with cationic polymers. As a proof-of-concept, chitosan (A), a biocompatible natural polysaccharide soluble at low pH, was used as the cationic polymeric component. The presence of primary amine groups on the polymer can potentially react with the carboxylic acid group on the acidic polar head group and will facilitate conjugation chemistry for the attachment of bioactive moieties. (B) Composite $AcLD_6$-chitosan hydrogels (on the right) are formed by mixing $AcLD_6$ (L) peptide (Ac-LIVAGD; SEQ ID NO: 65; dissolved in sodium hydroxide) with 1 kDa water soluble chitosan. At the same concentration, the peptide component dissolved in sodium hydroxide (control sample on the left) does not form hydrogels. (C) Hydrogel formation using different compositions of peptide and chitosan.

Figure 3:
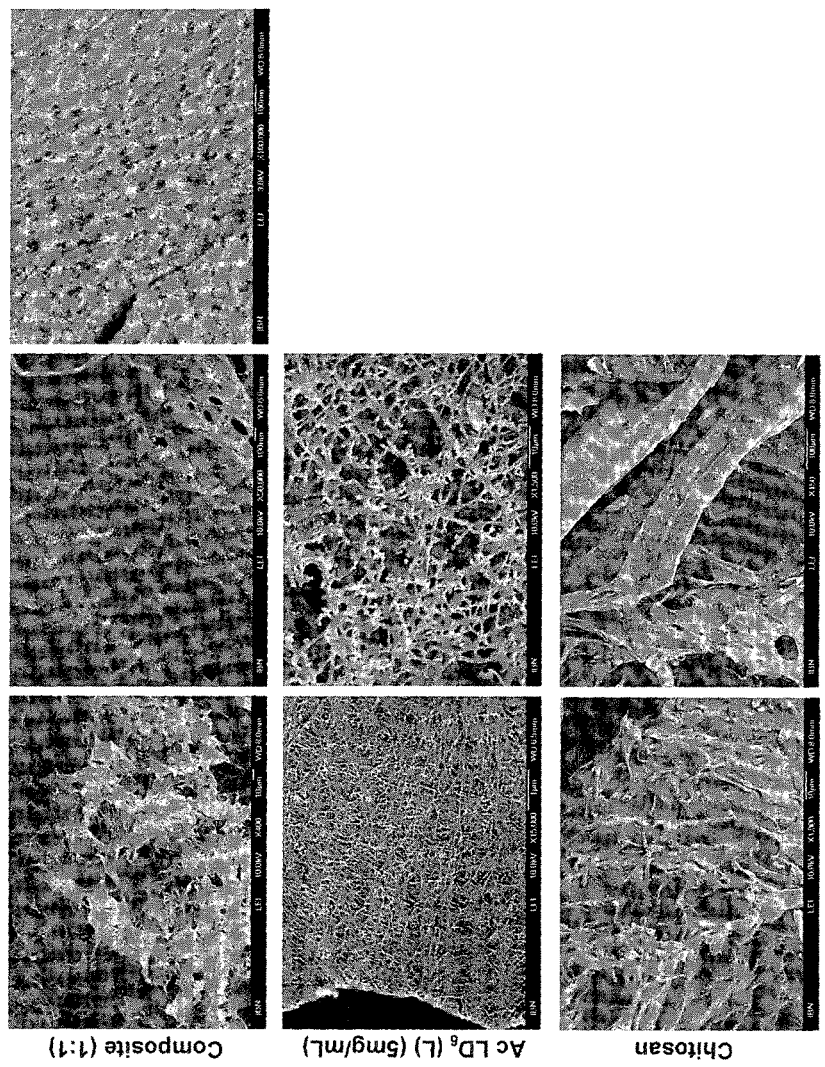

FIG. 3. Composite hydrogels retain the nanofibrous microarchitecture of pure peptide hydrogels, as observed under field emission scanning microscopy.

Composite hydrogel retains porous honeycomb structure, though nanoscale fibers are less defined. In comparison, the polymeric component did not demonstrate any fibrous architecture.

Figure 4:
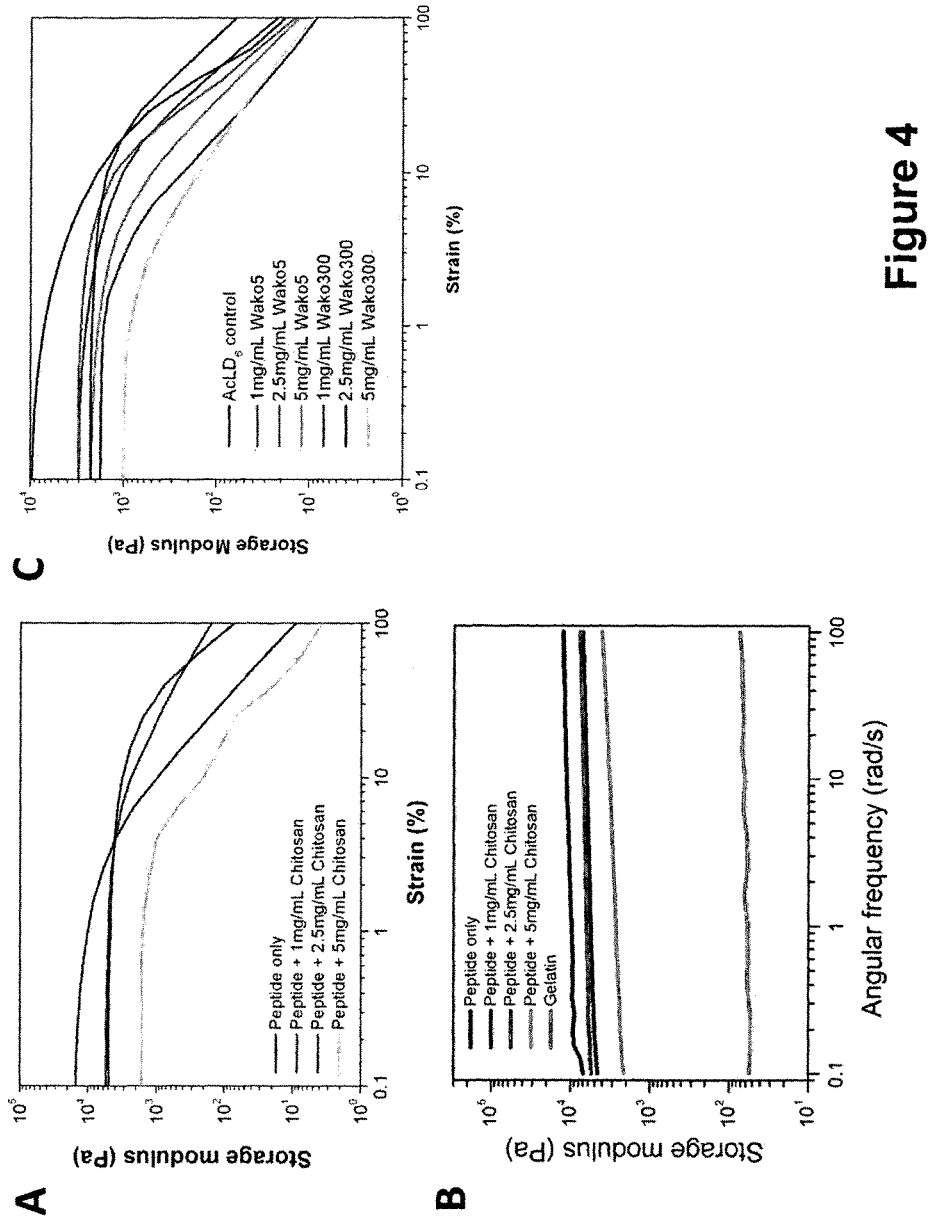

FIG. 4. Mechanical properties of composite hydrogel.

(A, B) Increasing chitosan concentration results in an increase in ability to tolerate strain (elasticity) with a concomitant slight decrease in mechanical strength. (C) Increasing polymer length, wherein W300 is longer than W5, leads to slight compromise in mechanical strength and increase in ability to tolerate strain.

Figure 5:
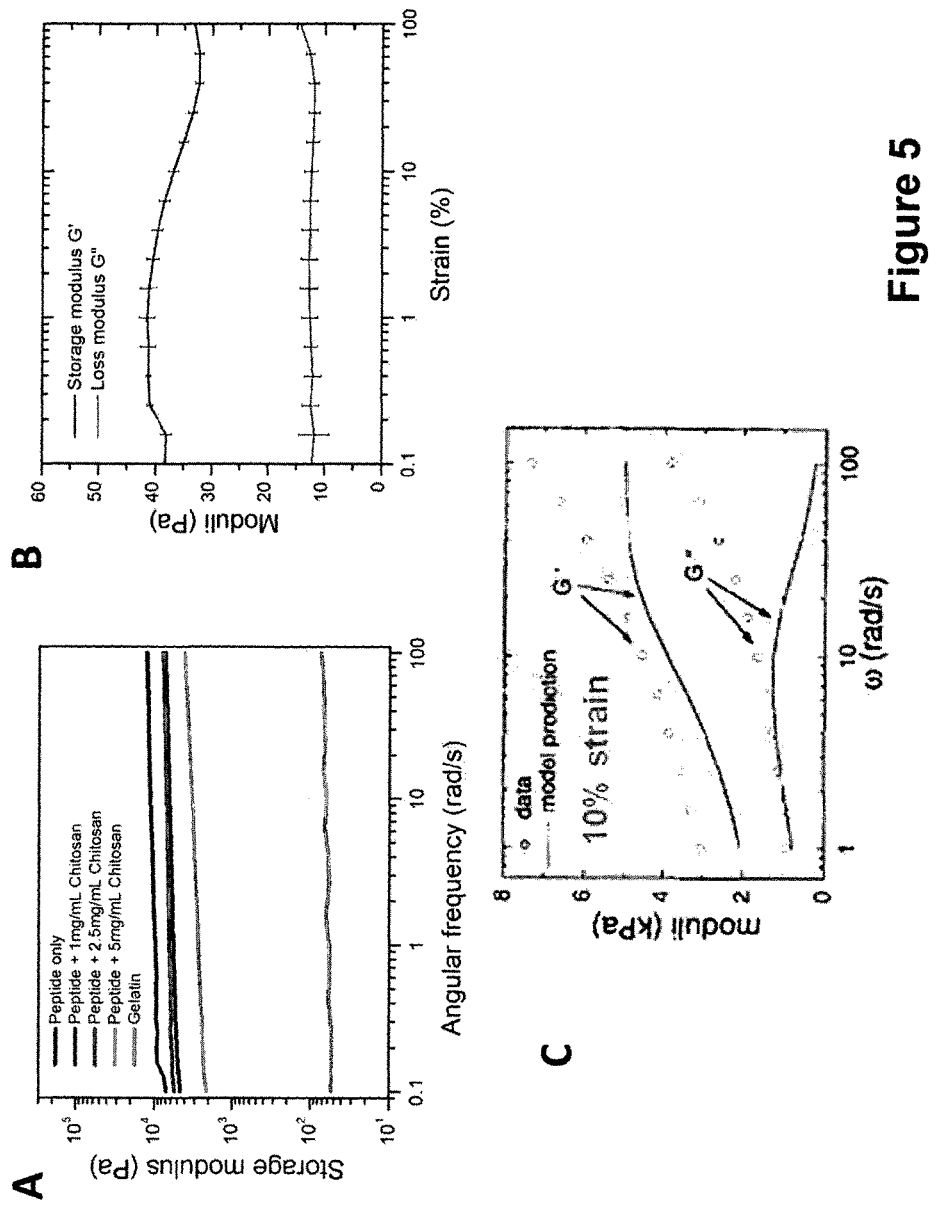

FIG. 5. Mechanical properties of composite hydrogel as compared to those of nucleus pulposus (NP).

Composite peptide-polymer hydrogels (A) have comparable mechanical stiffness to that of human NP(C). Peptide hydrogels are significantly stronger, but not as elastic. Thus the polymeric component can be used to modulate the mechanical properties to match that of native tissue. Porcine NP (B) is 20 times weaker than human (C). This could be attributed to differences in instruments used for measurements and experimental techniques.

Figure 6:
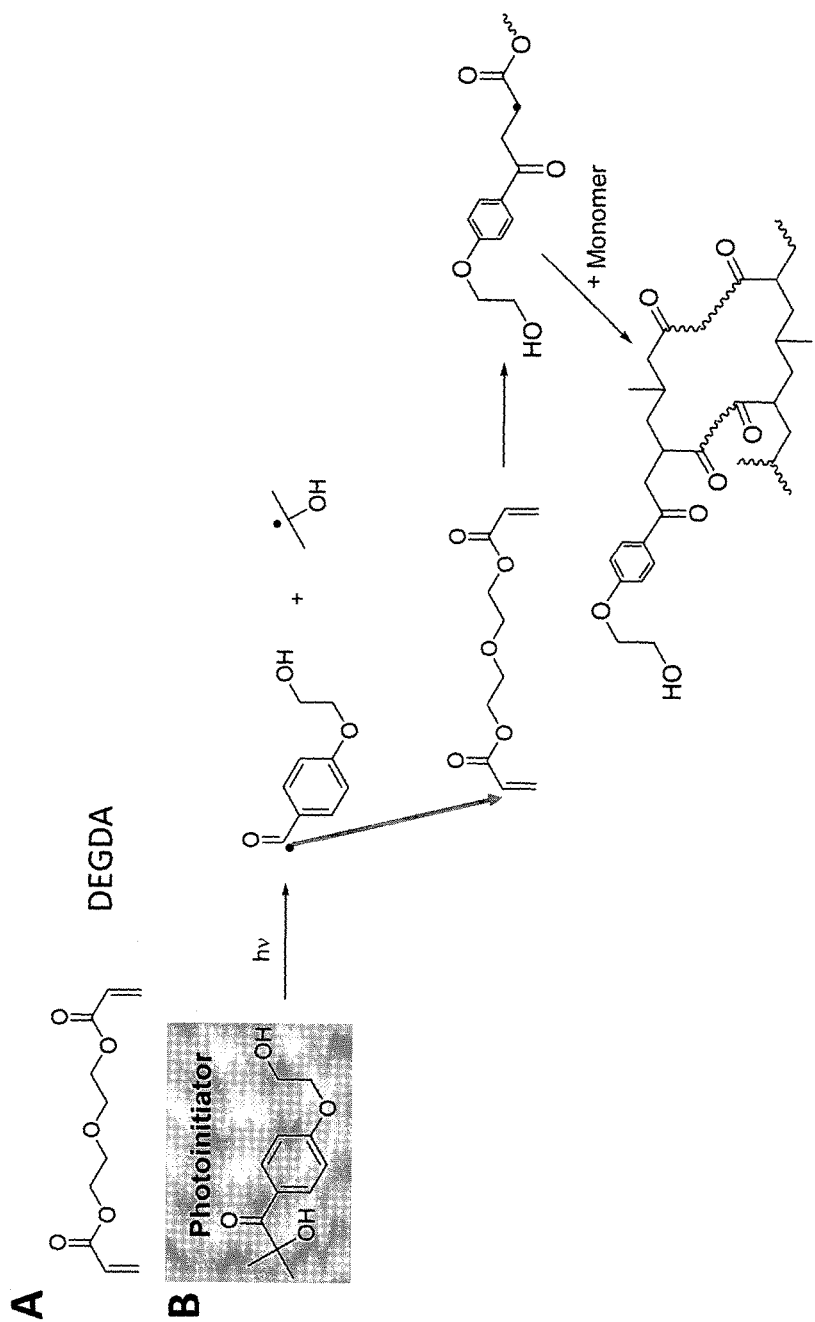

FIG. 6. Ultrashort peptide-neutral polymer composite hydrogels amendable to photo-initiated crosslinking.

Ultrashort peptides with neutral polar head groups form stable composite hydrogels when mixed with neutral polymers. As a proof-of-concept, diethylene glycol diacrylate (DEGDA) mixed with $AcAS_6$ (L; Ac-AIVAGS; SEQ ID NO: 69) formed hydrogels at various compositions. To stimulate photo-initiated crosslinking, a photoinitiator such as Irgacure 2959 (B) was added to the mixture. In the presence of ultraviolent light, the photoinitiator initiated a free-radical reaction, leading to the vinyl group of DEGDA being reactive towards neighbouring species.

Figure 7:
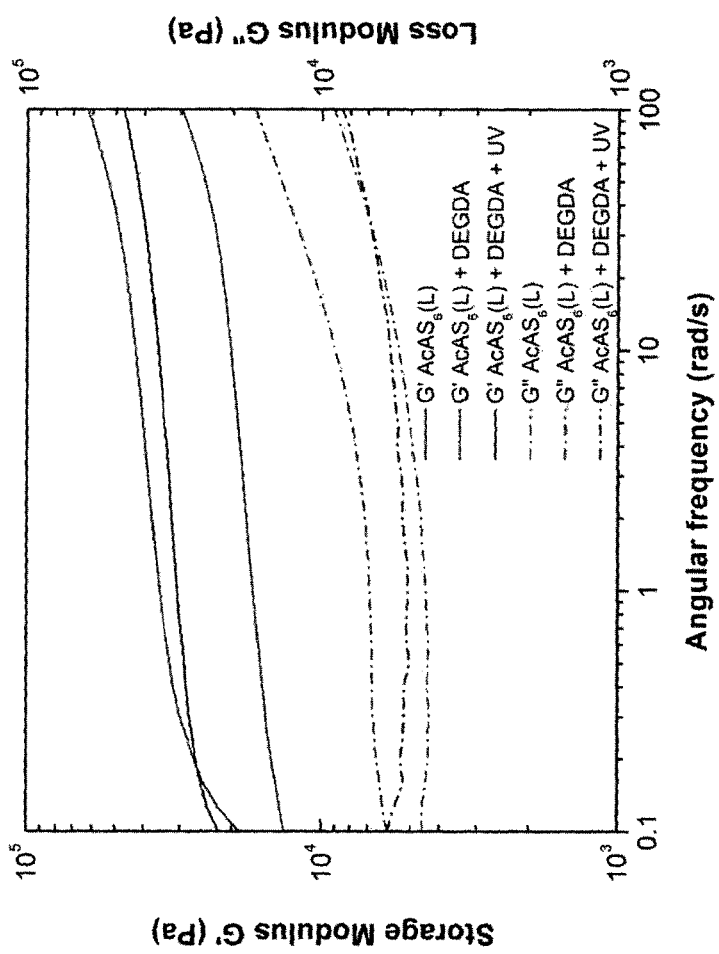

FIG. 7. Mechanical properties of composite peptide-DEGDA hydrogels, with and without photo-initiated crosslinking.

The addition of DEGDA (with and without photoinitiated crosslinking) enhanced the mechanical properties of $AcAS_6$, particularly the stiffness.

Figure 8:
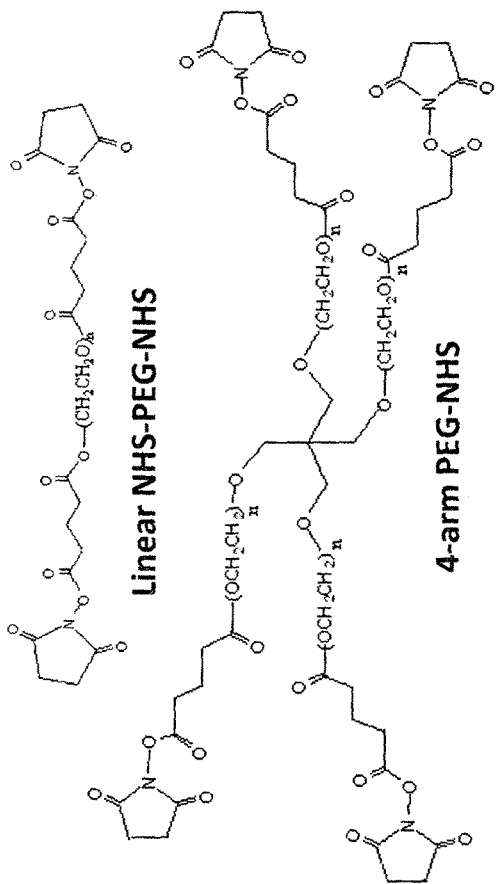
Figure 8:
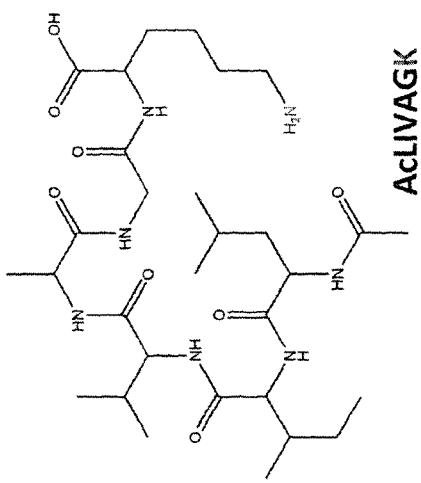
Figure 8:
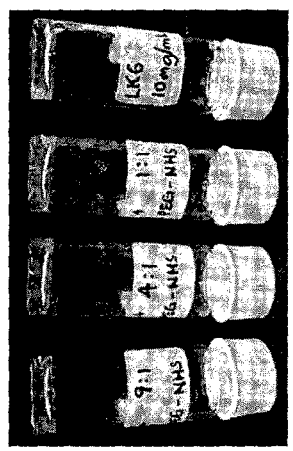
Figure 8:
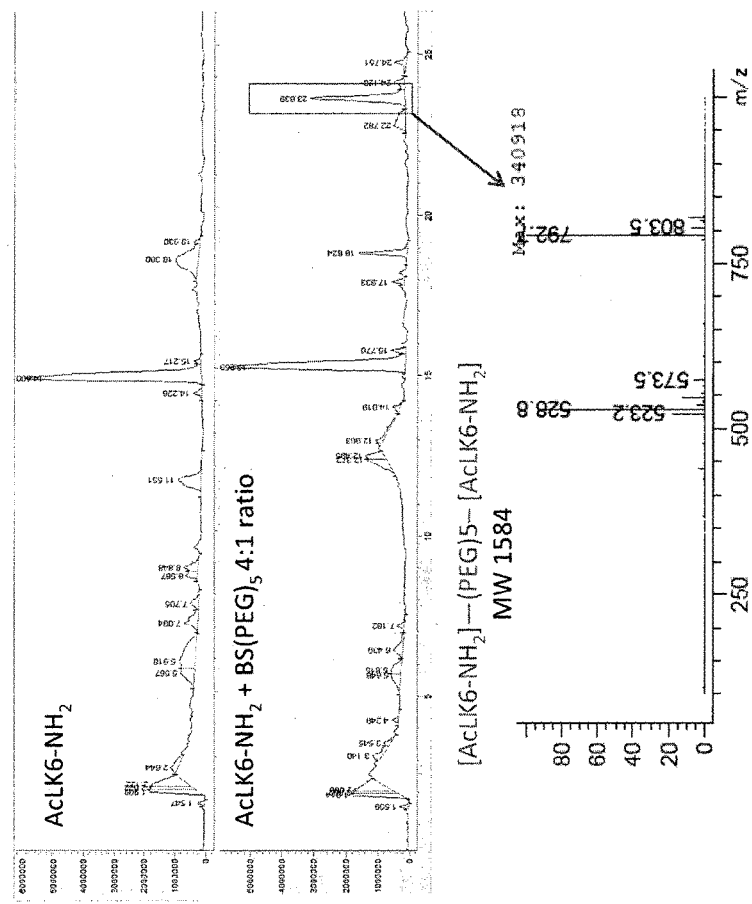

FIG. 8. Ultrashort peptide-neutral polymer composite hydrogels that can be covalently crosslinked.

Ultrashort peptides with basic polar head groups form stable composite hydrogels when mixed with neutral polymers. As a proof-of-concept, linear bi-functional PEG and branched multi-functional PEG were mixed with $AcLK_6$ (L; Ac-LIVAGK; SEQ ID NO: 66) peptides (A) to form composite peptide-polymer hydrogels at various compositions (B). The N-hydroxysuccinimide (NHS) functionality will react with the primary amine group on $AcLK_6$. Crosslinking between peptides are observed, as HPLC-MS analysis revealed the presence of the crosslinked species peptide-$PEG_5$-peptide (C).

Figure 9:
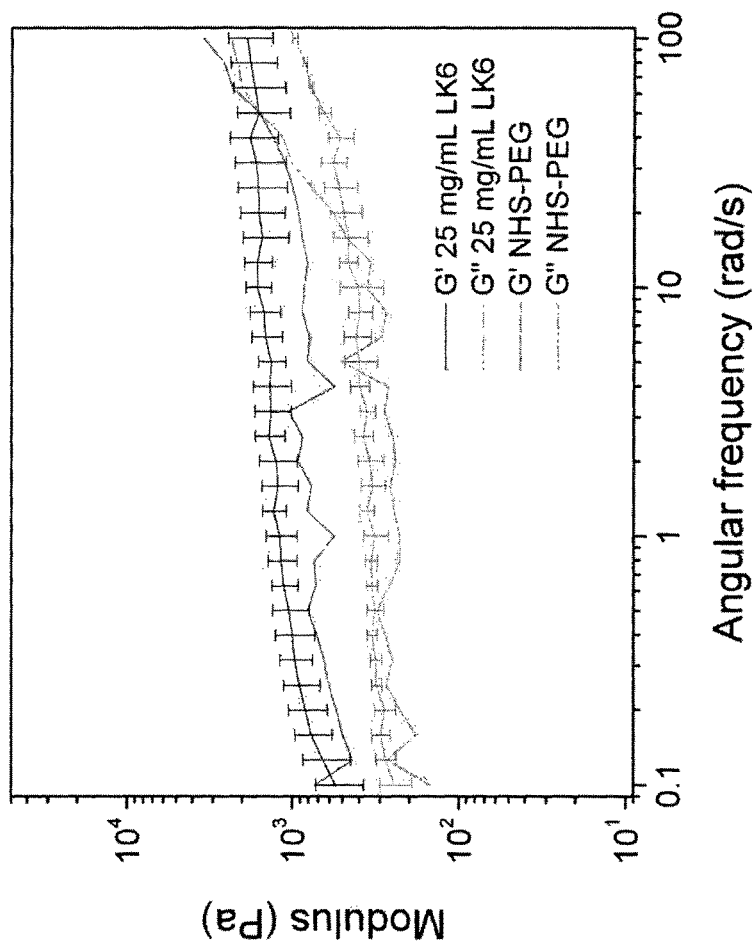

FIG. 9. Mechanical properties of composite peptide-PEG hydrogels.

The mechanical properties of the composite peptide-polymer (NHS-PEG) hydrogel are comparable to that of the peptide alone (25 mg/mL $AcLK_6$, i.e. Ac-LIVAGK; SEQ ID NO: 66).

Figure 10:
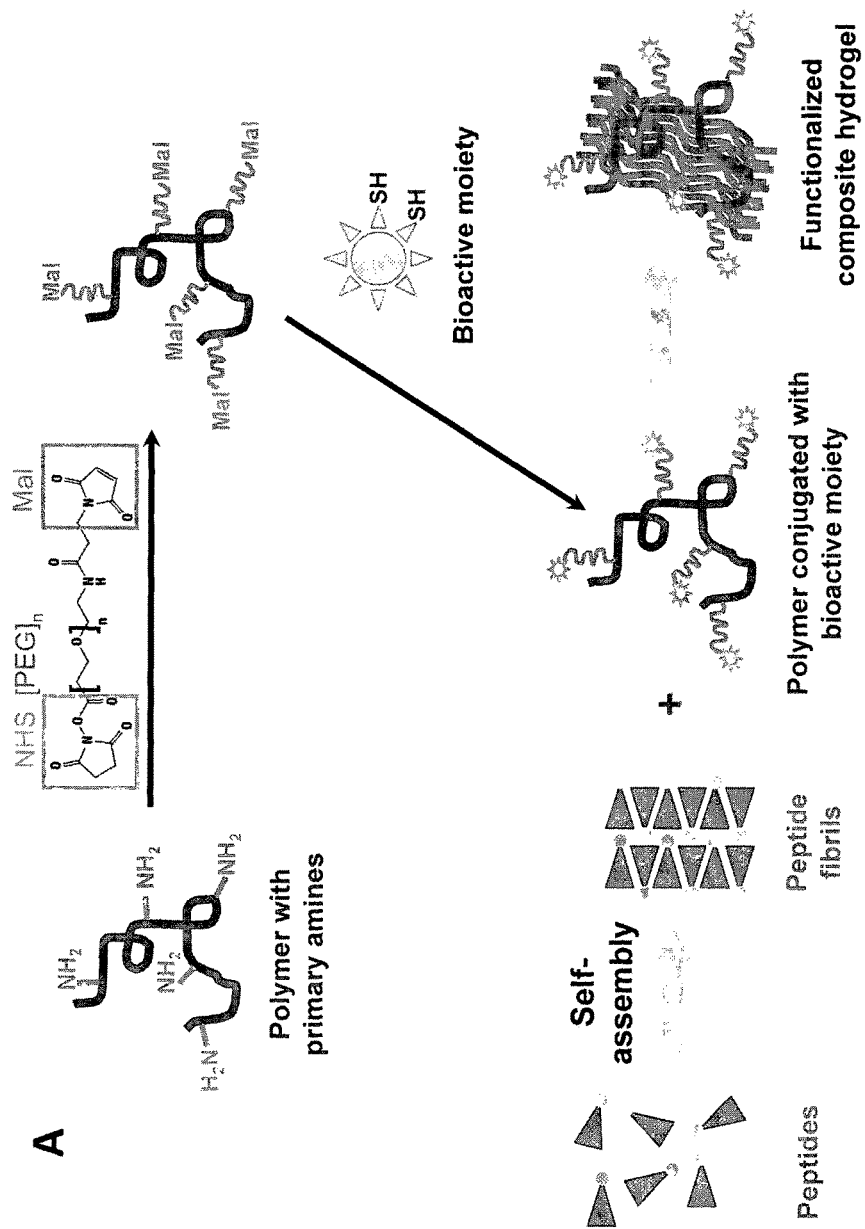
Figure 10:
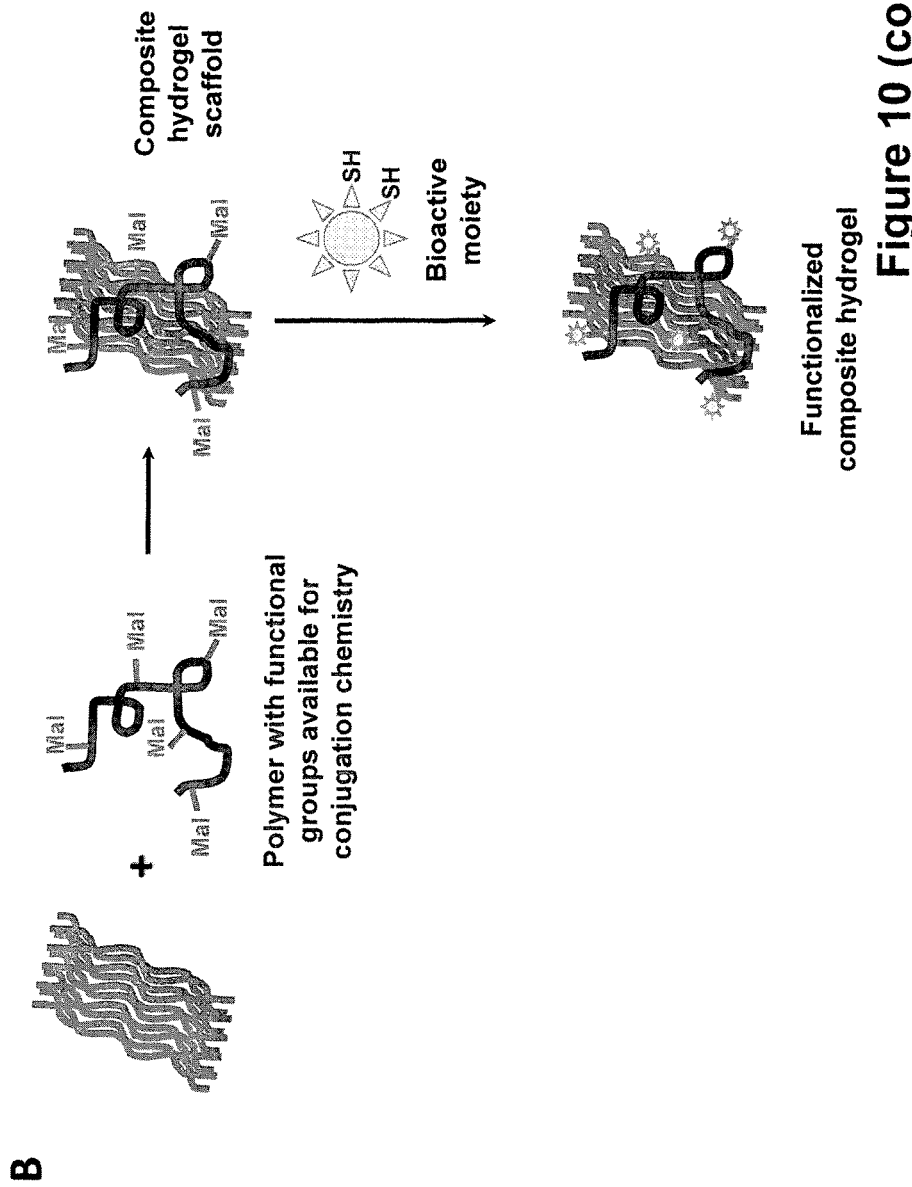

FIG. 10. Conjugation strategies for the immobilization of bioactive moieties such as growth factors.

Bioactive moieties can be immobilized onto composite peptide-polymer hydrogel by either mixing pre-conjugated polymer with self-assembling ultrashort peptides (A) or addition of the bioactive moiety post-gelation (B), where it will react with the relevant functional groups on the polymer. As a proof-of-concept, functional groups such as maleimide and primary amine groups can be exploited for conjugation using maleimide-thiol and NHS-amine chemistry.

Figure 11:
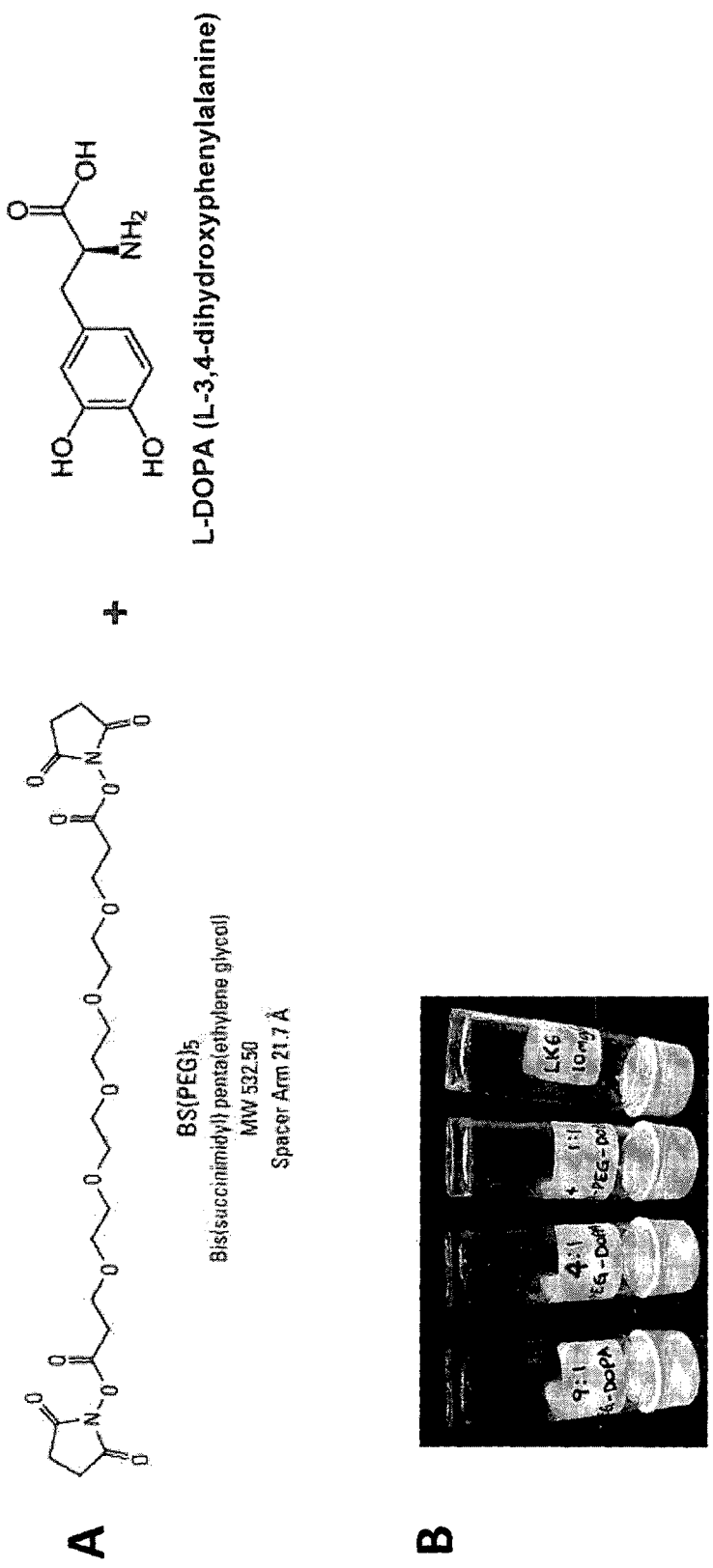
Figure 11:
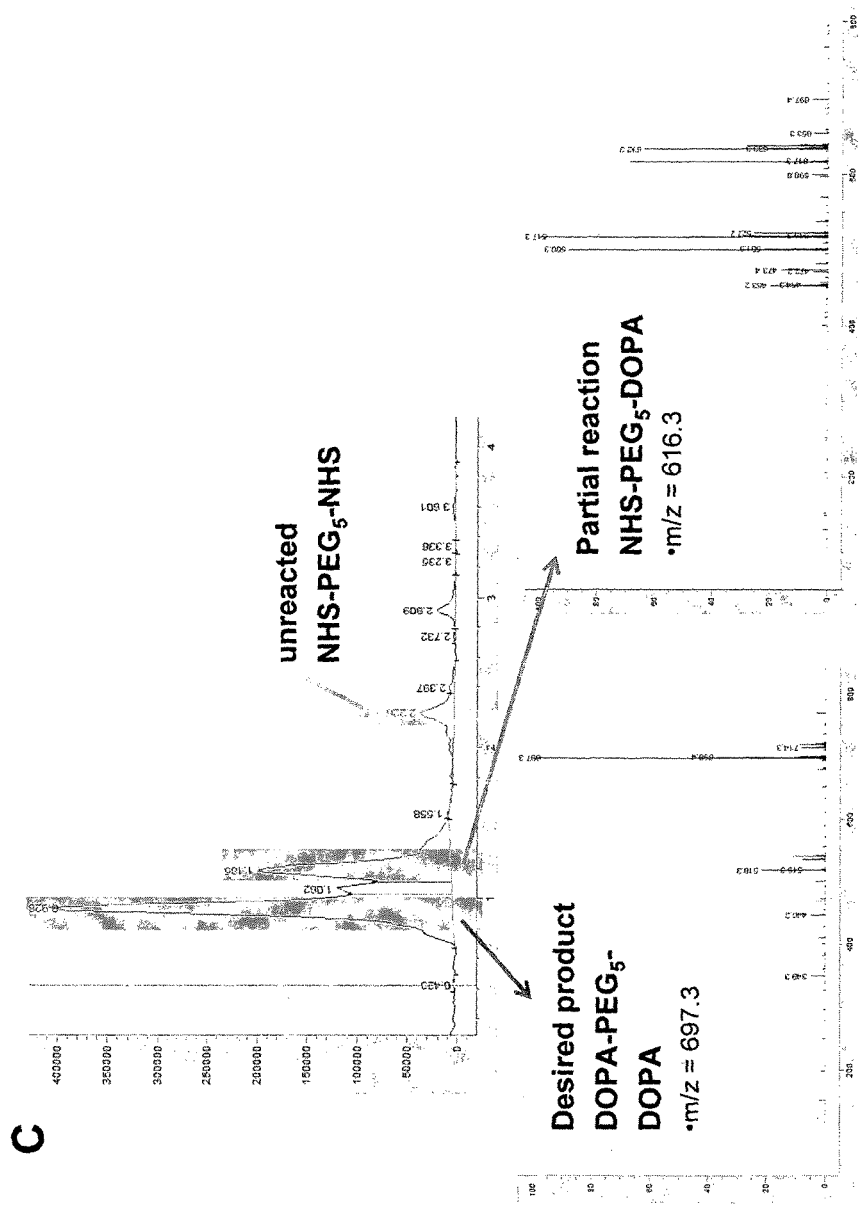

FIG. 11. Functionalized composite hydrogels formed by mixing functionalized polymers with ultrashort peptides.

As a proof-of-concept, a bioactive moiety (here: L-DOPA) was conjugated onto a linear bi-functional PEG polymer, bis(succinimidyl)PEG (BS-PEG), using NHS-amine chemistry (A). In lieu of the bi-functional BS-PEG, COOH-$PEG_n$-COOH can also be activated using carbodiimides, such as 1-ethyl-3-(3-dimethylaminopropyl) carbodiimide (EDC). In this example, DOPA-$PEG_5$-DOPA (C) was the functionalized polymer, and can be purified by centrifugation followed by dialysis, HPLC, or gel permeation chromatography (GPC). The completion of the reaction was determined using HPLC-MS. The functionalized polymer formed composite hydrogels with $AcLK_6$ (L; Ac-LIVAGK; SEQ ID NO: 66) at different compositions (B).

Figure 12:
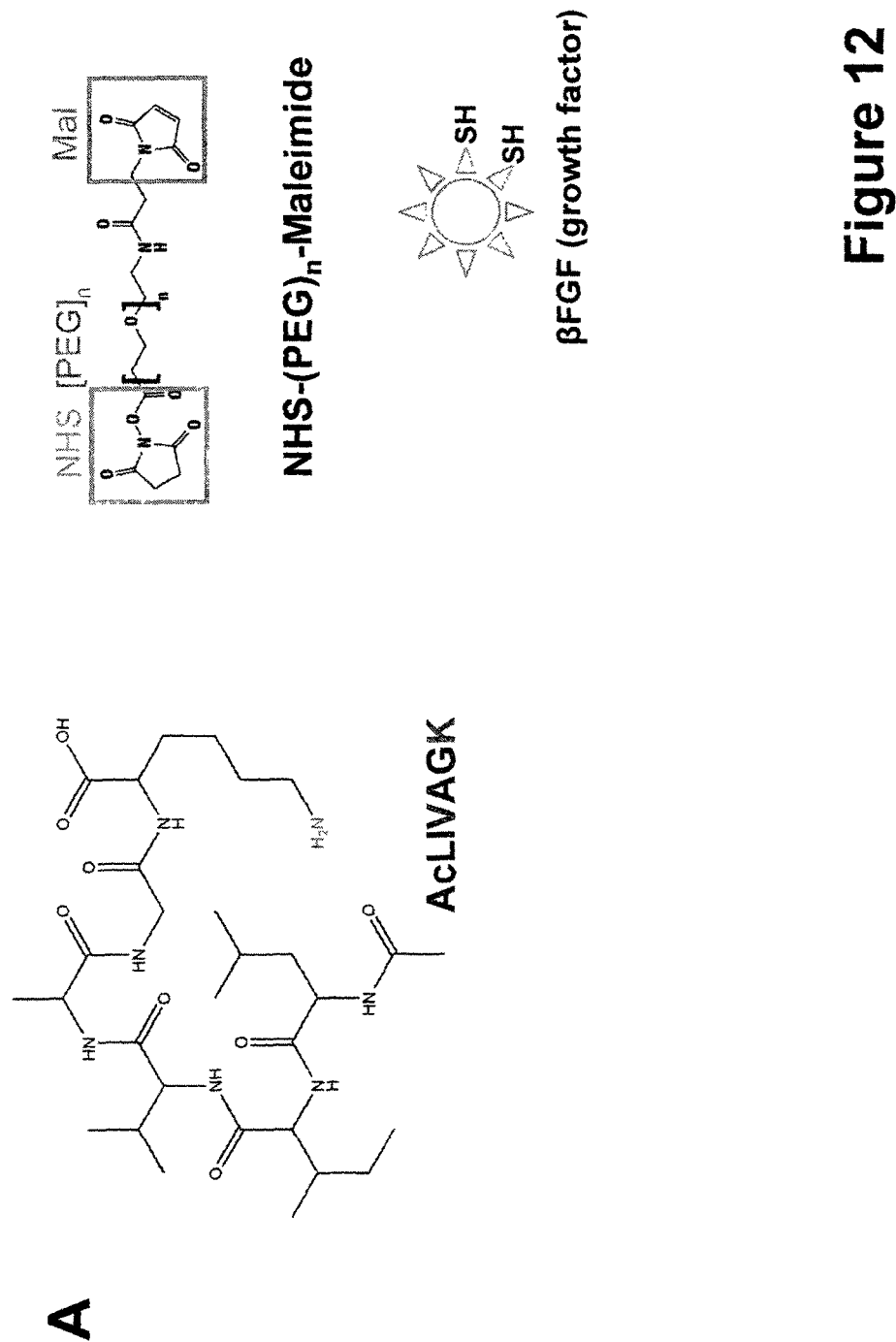
Figure 12:
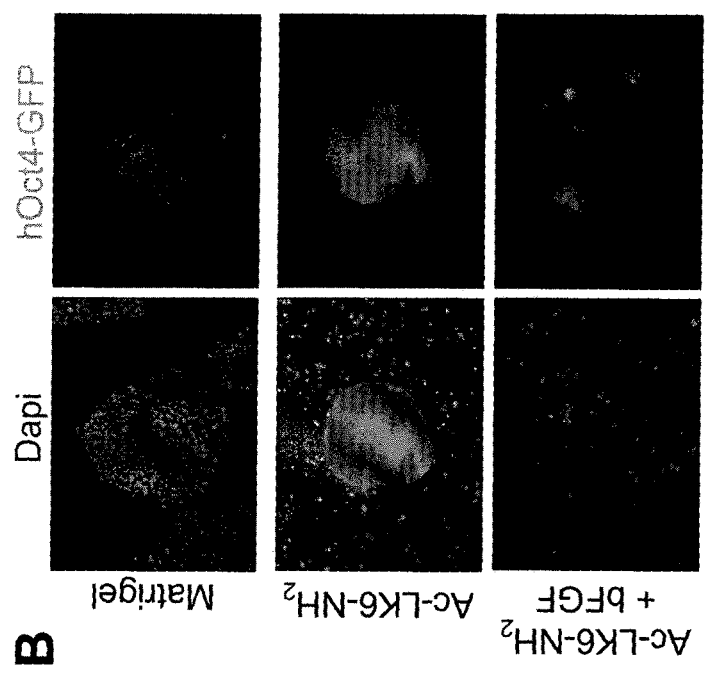
Figure 12:
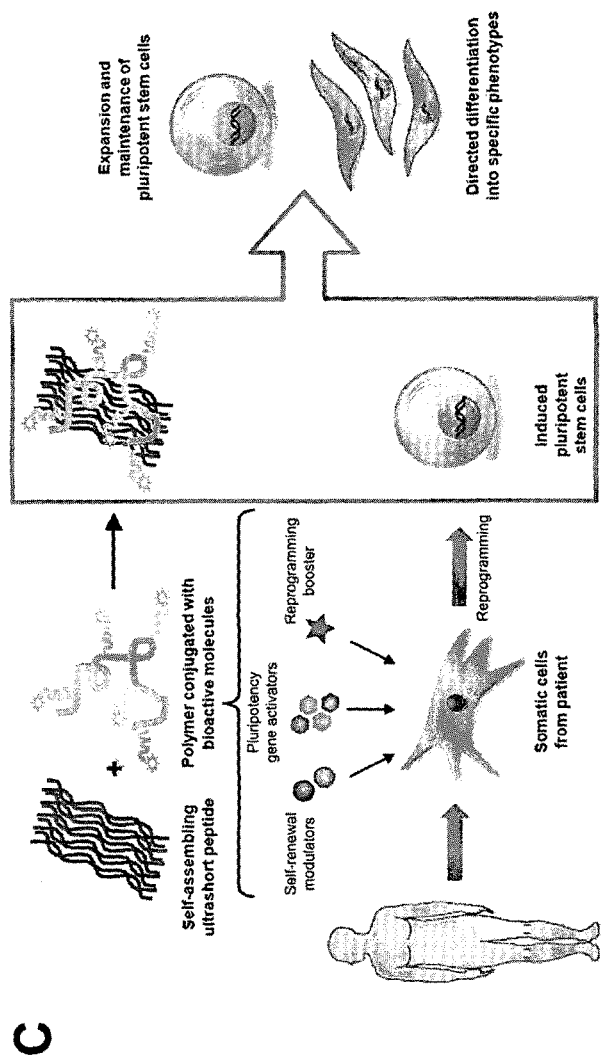

FIG. 12. Composite peptide polymer hydrogels functionalized with growth factor post-assembly.

As a proof-of-concept, a bioactive moiety in the form of a growth factor βFGF (needs to be defined?) was used to functionalize a composite (Ac-LIVAGK)-PEG composite hydrogel post-assembly. Hetero bi-functional PEG in the form of NHS-PEG-Maleimide (A) was used to form a composite peptide-polymer hydrogel either by mixing during hydrogelation or addition to a Ac-LIVAGK (SEQ ID NO: 66) hydrogel. Growth factors containing surface thiol groups (not needed for bioactivity), such as βFGF are then added to the composite hydrogel. The resulting functionalized composite hydrogel was evaluated as a synthetic cell culture substrate. The functionalization with βFGF enhanced the attachment of pluripotent embryonic stem cells (B). As compared to unmodified Ac-LIVAGK hydrogels, more but smaller colonies attached to the βFGF functionalized composite hydrogel. Furthermore, more of the cells maintained their pluripotency, as demonstrated by the higher hOct4-GFP (GFP needs to be defined?) expression (hOct4 is a marker for pluripotency). Such functionalized composite hydrogels can be further used to encapsulate bioactive small molecules for controlled sustained release. Applications include use as synthetic cell culture substrates, particularly for the large-scale or three-dimensional culture of stem cells (C). These multi-functionalized hydrogel scaffolds can potentially be used to maintain stem cell pluripotency (or multipotency) or to direct the differentiation into specific cell lineages, depending on the bioactive moieties immobilized and encapsulated.

Figure 13:
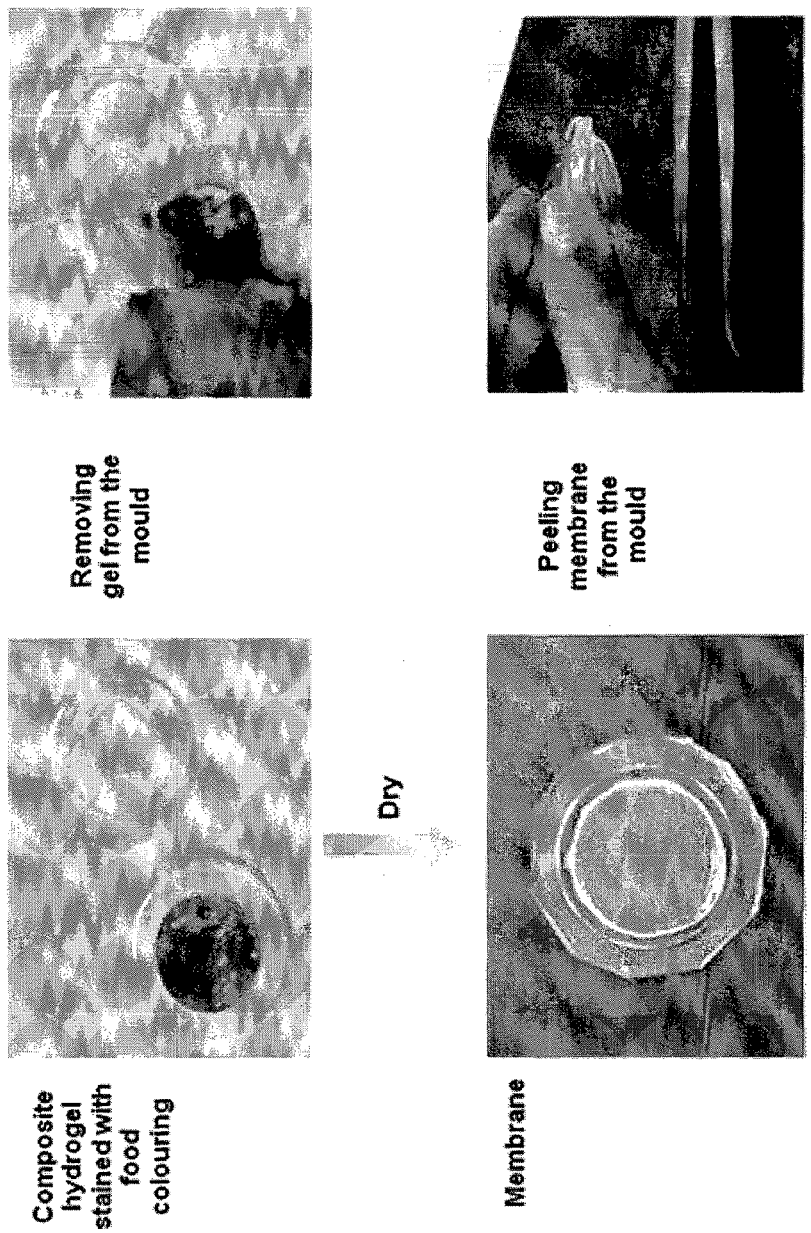

FIG. 13. The (pure) peptide and composite peptide polymer hydrogels can take on different forms (sol hydrogels, viscous gels and dried membranes) and can be molded into different three-dimensional shapes and sizes.

Small molecules such as dyes can be incorporated into the composite hydrogels as the solution mixture is poured into moulds. Following the gelation process, sol hydrogels are obtained. Moulds can be used to cast the hydrogels into specific three-dimensional shapes and sizes. When a sheet (or disc) of hydrogel is dried, membranes are obtained.

Figure 14:
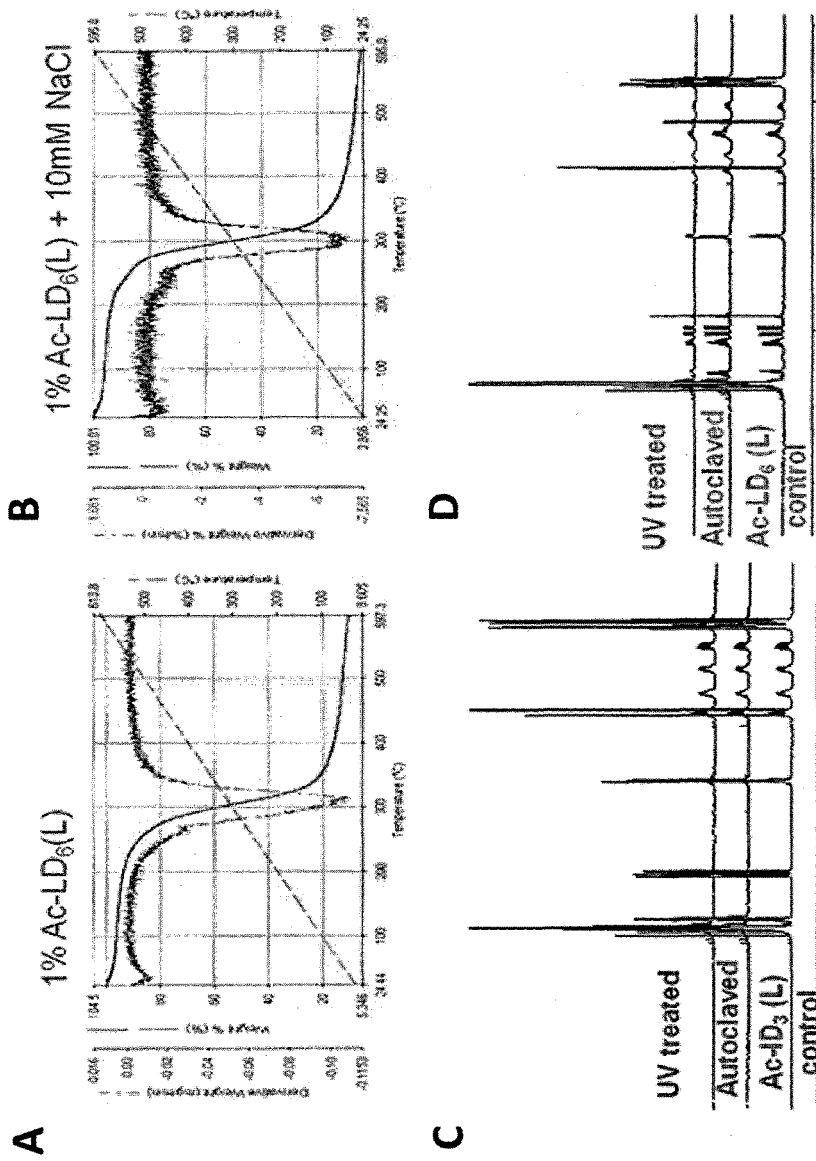
Figure 14:
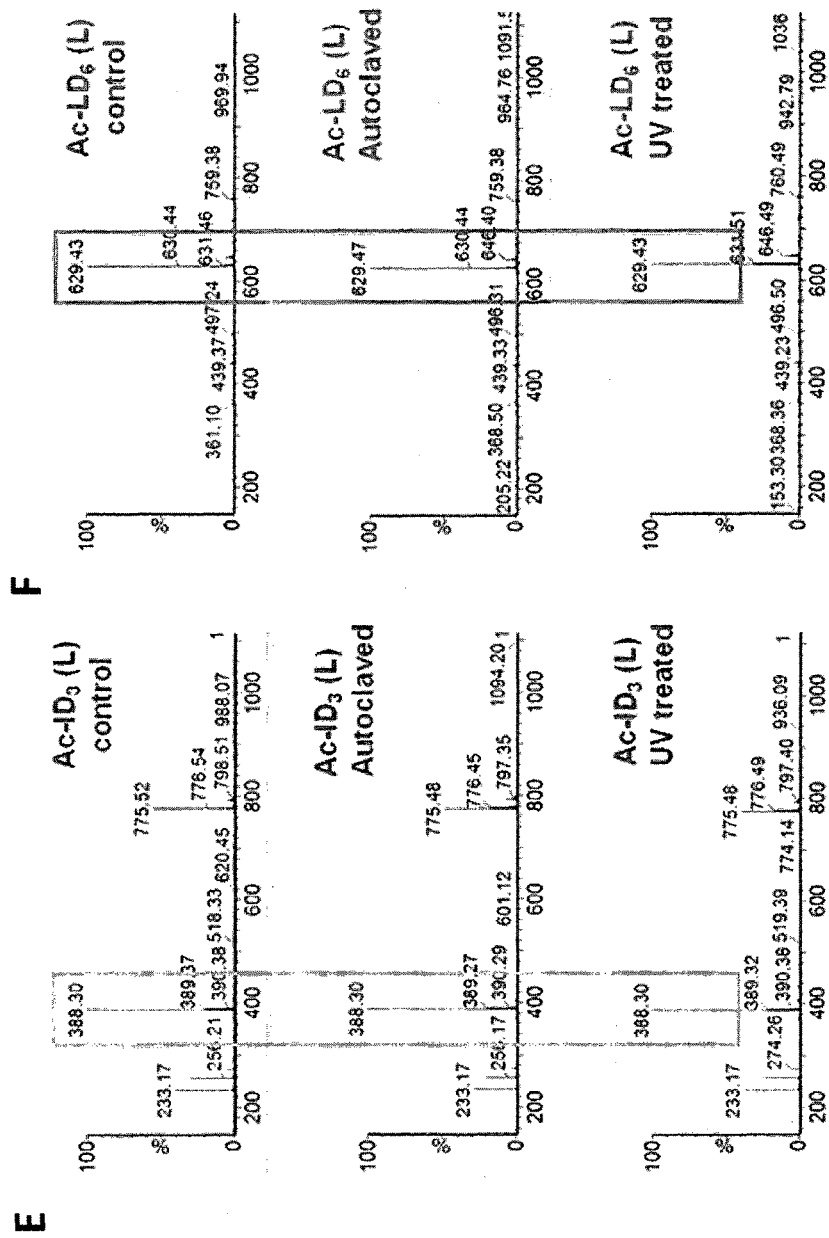

FIG. 14. Peptide stability studies.

TGA studies demonstrate high thermal stability of peptides (A) even in the presence of salts (B). Evaluation by $^1$H-NMR shows that peptides, exemplified by $AcID_3$, i.e. Ac-IVD (SEQ ID NO: 72), (C) and $AcLD_6$, i.e. Ac-LIVAGD (SEQ ID NO: 65), (D) do not decompose when UV treated (2 h, 254 nm) or autoclaved (30 min, 120° C.). HPLC-MS analysis indicates that the degradation of $AcID_3$ i.e. Ac-IVD (SEQ ID NO: 72), (E) and $AcLD_6$ i.e. Ac-LIVAGD (SEQ ID NO: 65), (F) following UV and autoclave treatment was minimal.

Figure 15:
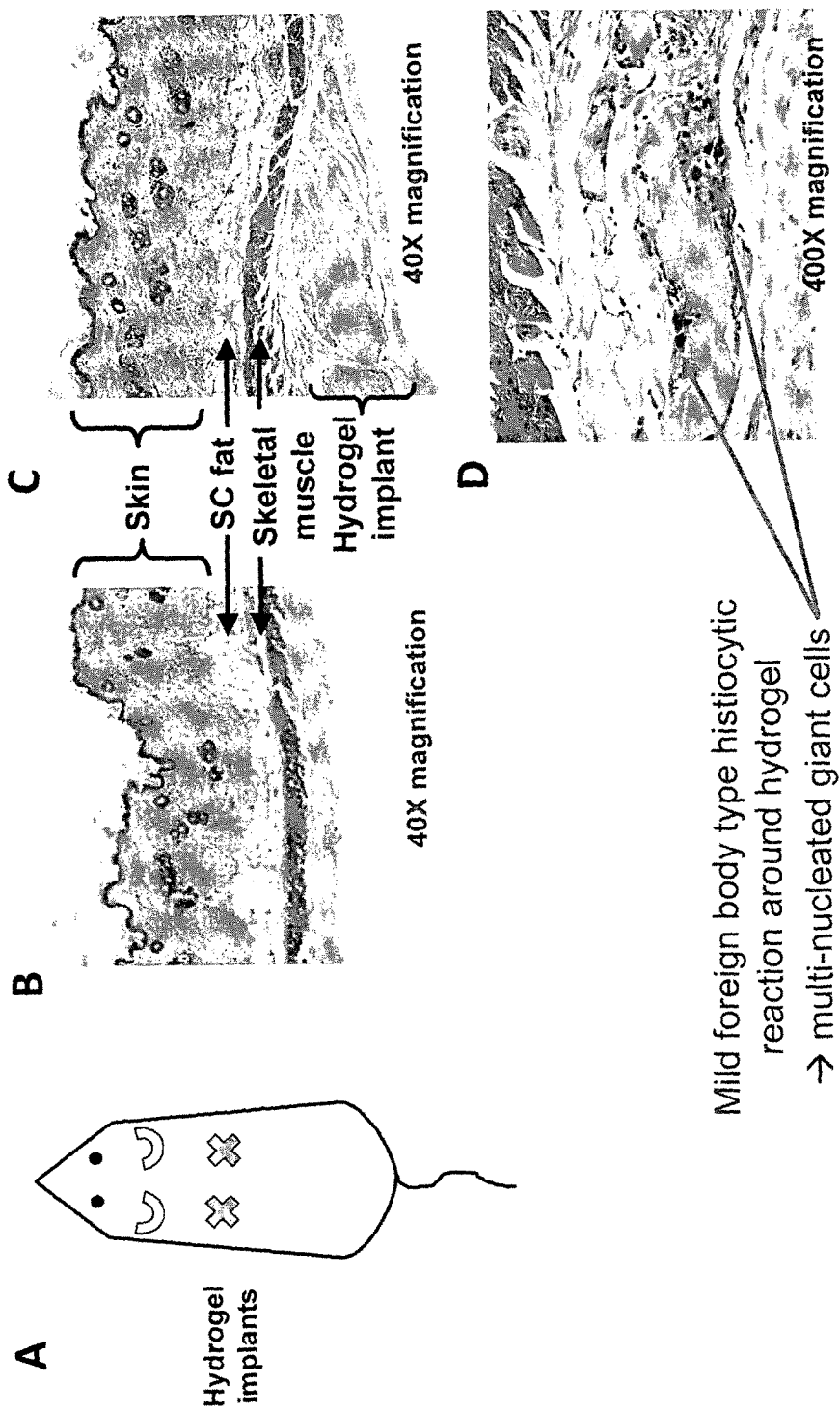

FIG. 15. In vivo biocompatibility of peptides.

In vivo biocompatibility was evaluated in C57BL/6 mice by implanting various hydrogels subcutaneously for up to two months (A). The hydrogel implant was stable and could still be detected after 2 months, as shown by the amorphous eosinophilic (pink) foreign body material beneath the skeletal muscle layer (B, C). Minimal to mild inflammatory reaction to subcutaneous hydrogel implants was observed, in the form of several multi-nucleated giant cells found at the peripheral of the implant (D). However, this is attributed to the surgery.

Figure 16:
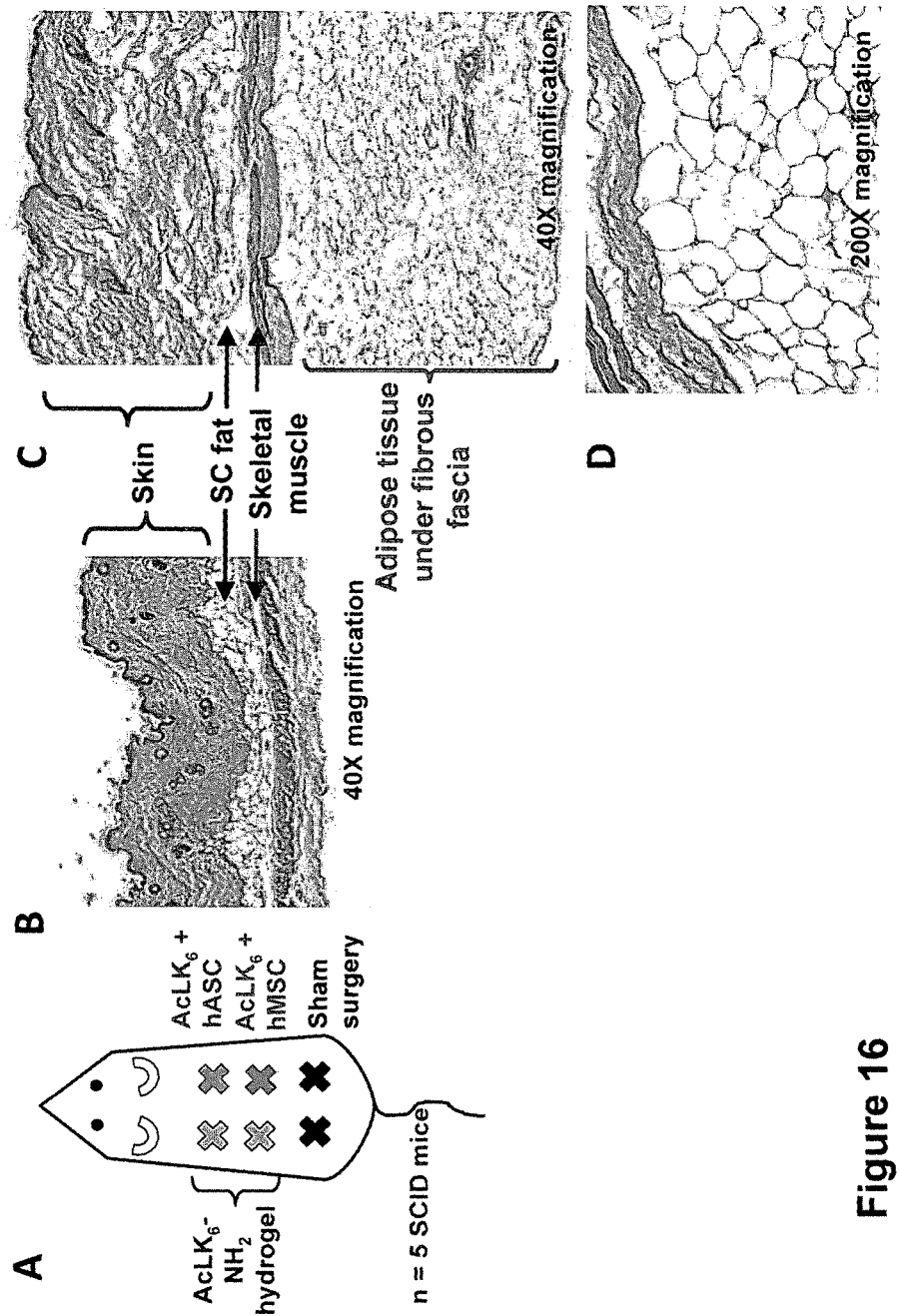

FIG. 16. In vivo scaffold for adipose tissue regeneration Fat pad observed under the skeletal muscle layer in the region of the human adipose stem cell (hASC) implant 45 days post-implantation (A-C). The transplanted cells have the appearance of normal mature adipose tissue (D)—adipocytes with dark nuclei at edge, cells filled with fat.

Figure 17:
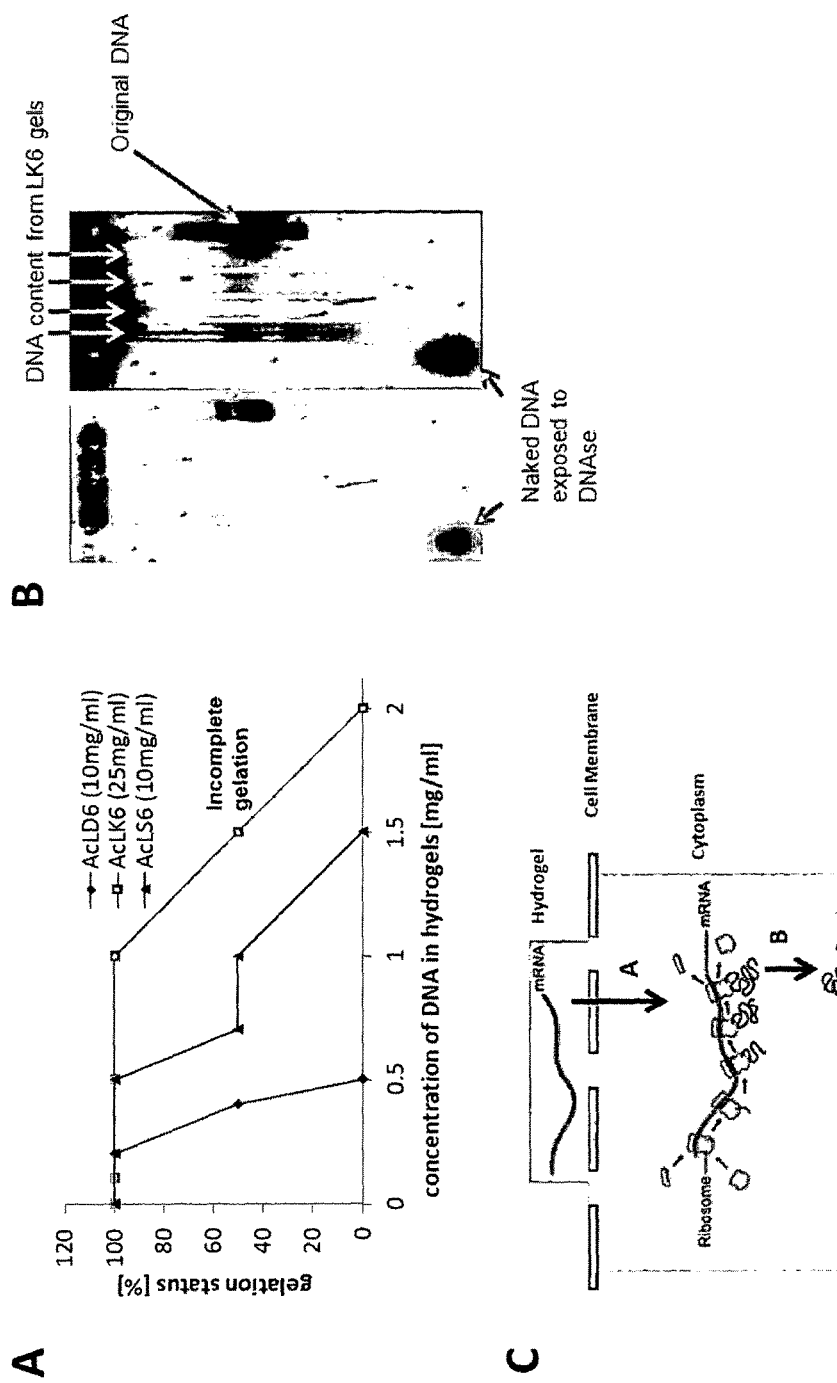

FIG. 17. Composite peptide-oligonucleotide hydrogels.

Various peptides ($AcLD_6$, i.e. Ac-LIVAGD, SEQ ID NO: 65; $AcLK_6$, i.e. Ac-LIVAGK, SEQ ID NO: 66; $AcLS_6$, i.e.

Ac-LIVAGS, SEQ ID NO: 67) were used to encapsulate plasmid DNA, forming composite peptide-DNA hydrogels (A). In particular the peptide AcLK$_6$ was extremely efficient in encapsulating and trapping the DNA, possibly through electrostatic interactions. There was minimal release of the DNA, as observed over the course of several days. AcLK$_6$ also effectively protected the DNA against nuclease degradation (B). When the composite hydrogels were incubated with DNAse, digested DNA fragments were not observed, compared to the naked DNA control. Compared to the original DNA fragment used to form the composite hydrogel, the composite hydrogel fragments did not migrate out of the well during electrophoresis, indicating that the peptide strongly interacts with oligonucleotides, increasing the mass and thereby hindering migration through the agarose gel. Potential applications include synthetic cell culture substrates that mediate sustained DNA, mRNA, siRNA and short hairpin RNA delivery (C).

EXAMPLES

In the course of our studies, different ultrasmall peptide and polymer combinations were used to demonstrate the feasibility and properties of the composite hydrogels. The formulation of each combination can further be optimized to alter the physical properties for different applications.

Example 1

Ultrasmall Peptide-cationic Polymer Composite Hydrogels

Ultrasmall peptides with an acidic polar head group, such as AcLD$_6$ (L) (i.e. Ac-LIVAGD; SEQ ID NO: 65), AcAD$_6$ (L) (i.e. Ac-AIVAGD; SEQ ID NO: 76) and AcID$_3$ (L) (i.e. Ac-IVD; SEQ ID NO: 72) form particularly stable composite hydrogels when mixed with (linear and branched) cationic polymers, such as chitosan and poly(amido amine) dendrimers (see Example 2 for more information). Gel formation is observed at higher pH compared to peptide only hydrogels. The stability of these composite hydrogels, as determined by their mass loss, in high salt conditions is also significantly improved. This observation suggests that the cationic polymers stabilize the hydrogels.

1. Formulation

As a proof of concept, the linear cationic polymer chitosan is used to demonstrate the feasibility of forming composite hydrogels with ultrasmall peptide AcLD$_6$ (L) (i.e. Ac-LIVAGD; SEQ ID NO: 65). The formation of the composite hydrogel depends on many factors—peptide concentration, polymer concentration, molecular weight and charge of the polymer, the presence of other salts and solvents.

Increasing peptide and chitosan concentration increases the ease of gel formation (FIG. 2). Chitosan also stabilizes gel formation at low peptide concentration. Furthermore, more stable composite hydrogels are formed when the molecular weight and concentration of the chitosan is increased. These gels require repeated "washing" in high salt conditions under agitation, for complete dissociation.

2. Microstructure of the Composite Scaffold

The microstructure of lyophilized composite hydrogels is observed under field-emission scanning microscopy (FE-SEM) as shown in FIG. 3. The composite hydrogel has a porous honeycomb microstructure, though the nanoscale fibres are less well-defined compared to peptide only hydrogels.

3. Mechanical Properties of the Composite Scaffold

The mechanical properties of the composite hydrogels are demonstrated in FIG. 4. The composite hydrogels are slightly weaker than peptide hydrogels, as reflected by a lower storage modulus. However, this is compensated by a dramatic increase in elasticity, from 0.5% strain to 5%. The gel strength decreases with increasing chitosan concentration. Increasing the polymer length further increases the elasticity of the composite hydrogel.

The mechanical properties of the composite hydrogel can be tuned by varying the composition. This is attractive for clinical applications, in which the gel strength can be varied to match that of tissue to be repaired, such as that of the nucleus pulposus (FIG. 5) to design an implant or an injectable therapeutic agent for degenerative disc disease or a dermal filler injected intradermally.

4. Moulding into Three-Dimensional Macroshapes and Casting Membranes

While the composite mixture is still in liquid phase, it can be poured into moulds before gelation occurs. The resulting composite hydrogel adopts the shape of the mould, enabling three-dimensional macrostructures such as discs and cubes, as shown in FIG. 13. As the surface of the moulds have been treated, the composite hydrogels can be easily unmolded without compromising their macroshape. When discs of composite hydrogels are dried, membranes are obtained.

5. Incorporating Bioactive Therapeutics

Bioactive therapeutics such as growth factors, cell adhesion molecules and prodrugs can be incorporated into the composite hydrogel by encapsulation (in the bulk phase) or by conjugation. Cationic polymers enhance the encapsulation of negatively charged molecules, such as oligonucleotides (plasmid DNA, messenger RNA, small interfering RNA); thereby increasing the loading capacity of the hydrogels. To conjugate bioactive molecules onto the polymer, functional groups, such as primary amines, on the polymer can exploited. Polyethylene glycol (PEG) crosslinkers, such as bi-functional or multi-functional polyethylene glycol (PEG), can be used to conjugate the bioactive moiety of interest to either the peptide or the polymer. The use of such linkers will enable the flexible movement of the conjugated moiety, facilitating cell recognition or allowing the moiety to adopt its ideal confirmation for therapeutic efficacy. FIG. 10 demonstrates a schematic for immobilizing growth factors onto the composite hydrogel. These gels can be subsequently deployed as drug delivery devices, cell culture substrates and implants for tissue regeneration.

Example 2

Ultrasmall Peptide-functionalized Polymer Composite Hydrogels Incorporating Branched Polymers Branched polymers can also be used to formulate stable composite hydrogels when mixed with different ultrasmall peptides. In particular, synthetic, functionalized water-soluble polymers such as dendrimers offer unique properties and advantages with respect to functional group variation, molecular weights, polarity, and structural diversity. The possibility of adding different functional end groups, such as amines, carboxylic acids, thiols, alcohols, and carbohydrates offer attractive material and chemical properties, as well as conjugation strategies to immobilize bioactive molecules. The number of functional groups can easily be adjusted, and therefore the concentration of the therapeutic molecules of interest within the gel can also easily be modified and fine-tuned.

Dendrimers belong to a large class of molecules with discrete structural diversities, characterized by the specific dendrimer generation. This diversity can range over several generations, seen by the amount of functional groups that increases per generation. Each generation is characterized by its initiator core. The amount of functional groups is determined by the structure of the initiator core. Starting with two functional groups in the first generation, the number of functional groups increases with $2^n$, where n corresponds to the type of generation. Hence, the second generation has four functional groups, and so forth. The characteristic branching of dendrimers limits the rate at which the therapeutic molecule will leach out of the gel, enabling controlled and sustained release.

Example 3

Ultrasmall Peptide-neutral Polymer Composite Hydrogels

Ultrasmall peptides with various (acidic, basic, neutral) polar head groups formed stable composite hydrogels when mixed with uncharged polymers such as polyethylene glycol (PEG).

1. Formulation

As a proof-of-concept, di(ethylene glycol)diacrylate (DEGDA) forms composite hydrogels with ultrasmall peptides $AcAS_6$ (L) (i.e. Ac-AIVAGS; SEQ ID NO: 69), $AcLS_6$ (L) (i.e. Ac-LIVAGS; SEQ ID NO: 67), $AcLT_6$ (L) (i.e. Ac-LIVAGT; SEQ ID NO: 68), and $AcLD_6$ (L) (i.e. Ac-LIVAGD; SEQ ID NO: 65). The formation of these composite hydrogels depends on peptide concentration, PEG concentration and molecular weight, and the presence of other solvents.

Photoinitiators such as Irgacure 2959 and 369 (from BASF) can be incorporated into the composite $AcAS_6$-DEGDA (i.e. Ac-AIVAGS; SEQ ID NO: 69), hydrogels (FIG. 6). Following UV irradiation, the gels change in appearance from clear/translucent to opaque.

The mechanical properties of the $AcAS_6$-DEGDA Ac-AIVAGS; (i.e. Ac-AIVAGS; SEQ ID NO: 69), composite hydrogel are comparable to that of $AcAS_6$ (i.e. Ac-AIVAGS; SEQ ID NO: 69), peptide hydrogels (FIG. 7).

By pouring the liquid mixture of peptide and PEG into moulds prior to gelation, three-dimensional composite hydrogels can be obtained.

Using moulds that permit UV transmission, composite scaffolds can be formed by irradiating peptide-DEGDA composite gels containing photoinitiator. The resulting structures retain their shapes and do not collapse into membranes even after the removal of the water by evaporation.

2. Formulation of Chemically/Covalently Crosslinked Composite Hydrogels

As a proof-of-concept, bi-functional PEG with two (terminal) N-hydroxysuccinimide (NHS) groups forms composite hydrogels with ultrasmall peptides $AcLK_6$ (L) (i.e. Ac-LIVAGK; SEQ ID NO: 66), $AcIK_6$ (L) (i.e. Ac-ILVAGK; SEQ ID NO: 71), $AcAK_6$ (L) (i.e. Ac-AIVAGK; SEQ ID NO: 70), $AcIK_3$ (L) (i.e. Ac-IVK; SEQ ID NO: 73), $AcLK_3$ (L) (i.e. Ac-LVK; SEQ ID NO: 74) and $AcAK_3$(L) (i.e. Ac-AVK; SEQ ID NO: 75). The extent of crosslinking depends on the ratio of polymer to peptide, as well as the number of functional groups available for reaction. The extent of crosslinking can be detected and quantified using mass spectrometry.

3. Formulation of Composite Hydrogels with Immobilized Growth Factors

As a proof-of-concept, a solution of hetero bi-functional NHS-PEG-maleimide polymer was added to pre-formed Ac-LIVAGK (L) (SEQ ID NO: 66) hydrogels (FIGS. 8 to 10). After allowing for the polymer to diffuse into the gel and for the NHS functional group to react with the primary group on Ac-LIVAGK (L), β-FGF was added (FIG. 12). The maleimide on the polymer would then react with a free sulfhydryl group on the surface of the growth factor. The resulting hydrogel demonstrated improved cell adhesion characteristics, resulting in greater numbers of embryonic stem cell colony attachment.

Example 4

Ultrasmall Peptide-Oligonucleotide Composite Hydrogels

Ultrasmall peptides of different amino acid sequences and (acidic, basic, neutral) polar head groups formed stable composite hydrogels when mixed with aptamers and oligonucleotides, such as plasmid DNA, messenger RNA and small interfering RNA (siRNA). These composite hydrogels are unique in that the "polymer" is also the bioactive molecule of interest.

1. Formulation

Plasmid DNA is used to demonstrate the feasibility of forming composite hydrogels with different peptide sequences. The peptide sequence (particularly the polar head group) and concentration plays a significant role in determining the maximum amount of DNA that can be incorporated into the composite hydrogel. Peptides with basic (C-terminal) head groups, such as $AcLK_6$ (L) (i.e. Ac-LIVAGK; SEQ ID NO: 66), could integrate the highest concentration of DNA. Peptides with acidic head groups such as $AcLD_6$ (L) (i.e. Ac-LIVAGD; SEQ ID NO: 65) had the lowest threshold for DNA loading and further increases in DNA concentration resulted in incomplete or non-gelation.

2. Release of the Oligonucleotides

Dissociation of the composite hydrogel, with the concurrent release of the DNA was minimal, as demonstrated in FIG. 17. Even after 10 days, at least 80% of the DNA loaded remained in composite hydrogel. In particular, the Ac-LIVAGK (L)-DNA hydrogel retained 95% of the DNA added. The release of the nucleic acid can potentially be modulated by the peptide composition. The DNA was also protected from degradation, which bodes well for the incorporation of the more labile messenger RNA. As the physical and chemical properties of DNA, messenger RNA and siRNA are comparable, it is reasonable to conclude that the incorporation efficiency and dissociation characteristics will be similar.

3. Applications

The present invention offers a package solution for patients on demand for therapies using tissue engineering, i.e. a package solution for patient-tailored cell therapy. The self-assembled composite ultrasmall peptide-polymer hydrogels of the invention provides an overall solution, starting from taking patient's healthy tissue, such as fibroblasts, and change it to the cell type where a therapy is needed.

By using messenger RNA that encodes for the Yamanaka factors in the composite hydrogel, re-programming of the somatic cells can be achieved without the use of viral vectors or repeated transfection. Messenger RNA encoding growth factors and transcription factors can be used to direct the differentiation of stem cells cultured on the composite hydrogel.

For clinical applications, messenger RNA encoding growth factors (to enhance regeneration of the tissue) or cytokines (to reduce inflammation) will facilitate recovery and localize the therapeutic effect, reducing undesirable systemic side effects.

Figure 1:
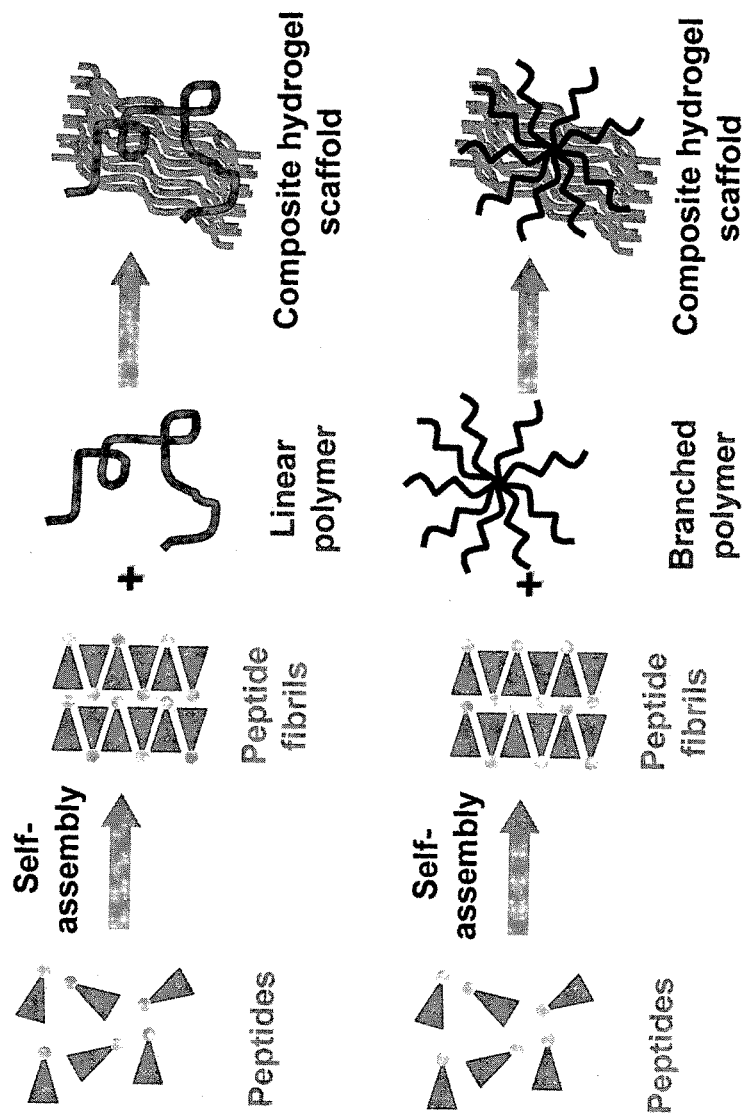
FIG. 1. Schematic of ultrasmall peptide polymer composite hydrogel formation.

According to FIG. 1, which shows the hypothesis of hydrogel formation, when the pH of acidic peptide hydrogels, such as hydrogels based on $AcLD_6$ (i.e. Ac-LIVAGD; SEQ ID NO: 65), is raised, some peptides ionize and diffuse away. The rationale of creating composite hydrogels is thus to "capture" the ionized peptides with cationic polymers, thereby stabilizing the hydrogel. As a proof of concept, the inventors have chosen chitosan. The inventors found that gelation depends on many factors, of which the most important is the type of chitosan used. Screening seven different chitosans, the inventors identified three candidates for further rheological evaluation. The first was a water soluble chitosan with molecular weight around 1 kDa. The latter two candidates were mid and high-molecular weight chitosans. These three chitosans formed composite hydrogels which were more stable in PBS, though with repeated washing steps, they also dissociated. This suggests that the change in ionic environment can be applied to retrieve cells cultured in the hydrogel, eliminating the use of enzymes.

According to FIG. 4, the composite hydrogels were slightly weaker than peptide hydrogels and the storage modulus decreased with increasing chitosan concentration. However, there was a dramatic increase in elasticity, from 0.5% strain to 5%, making them more attractive for in vivo applications. Increasing the polymer length further increased the elasticity of the composite hydrogel.

For tuning the properties of their peptide hydrogels to that of native tissue, the inventors first determined the mechanical properties of nucleus pulposus. Using the pig as a large animal model, the inventors found that the storage modulus of porcine nucleus pulposus is 20× weaker than published data for humans (FIG. 5). This could be attributed to humans being upright and hence our spinal column would experience more compressive forces. The inventors also found that the age of the animals did not make a significant difference in their elastic properties, unlike for humans. The hydrogels of the present invention are significantly stronger, though much less elastic with yield points of 0.5% strain compared to 2% for porcine tissue.

Example 5

Injection Therapy and Implants

The composite polymer-peptide hydrogels can form the basis of an injectable therapy wherein the mixture injected as a solution will gel in situ upon injection into the body. For instance, for degenerative disc disease, the treatment will be applied to the nucleus pulposus; while for urinary incontinence, the injection will be applied to the wall of the urethra. Such treatments are minimally invasive (not requiring surgery) and provide mechanical support to the degenerated tissue.

Subcutaneous implantations of $AcLK_6$ (i.e. Ac-LIVAGK; SEQ ID NO: 66) hydrogels seeded with human derived adipose stem cells into nude mice, resulted in the formation of fat pads under the implant site after 45 days (FIG. 16). This suggests that the hydrogels can be applied as dermal fillers and scaffolds for adipose tissue transplantation/regeneration.

Subcutaneous implants of various peptide hydrogels in mice did not cause any significant immunogenic or physiological reactions. There were no behavioral changes or weight loss following implantation for up to 2 months, and there was no significant difference in red or white blood cell counts or blood chemistry (liver and kidney function) between mice implanted with hydrogels and sham operated mice.

Using a guinea pig model, Kligman maximization assays were performed (by a contract research organization) for 12 ultrashort peptide candidates to date. Topical applications and intradermal injections of the various peptide hydrogels did not stimulate any irritation or allergic reactions after 24 hours. Subsequent immunologic challenges at day 27 also elicited no immune or allergic response. Likewise, no systemic toxicity was observed. This indicated that the peptides tested were non-immunogenic and the potential for stimulating an allergic response with repeated use is low.

TABLE 1

Pilot study with 4 mice (10 days)
implant = 30 µL Ac-LIVAGK (L) gel
5 mm diameter, 1 mm height

|  | normal range | un-treated | SCID 1 | SCID 2 | normal |
| --- | --- | --- | --- | --- | --- |
| neutrophils (K/uL) | 0.1-2.4 | 2.16 | 2.1 | 0.77 | 1.6 |
| lymphocytes (K/uL) | 0.9-9.3 | 0.89 | 0.88 | 0.9 | 3.76 |
| monocytes (K/uL) | 0-0.4 | 0.78 | 0.22 | 0.12 | 0.42 |
| eosinophils (K/uL) | 0-0.2 | 0.17 | 0.31 | 0.03 | 0.11 |
| basophils (K/uL) | 0-0.2 | 0.21 | 0.08 | 0 | 0.02 |
| thrombocytes (M/uL) | 6.36-9.42 | 1.01 | 0.607 | 0.978 | 0.833 |
| erythrocytes (M/uL) | 0.592-2.972 | 9.72 | 9.29 | 11.33 | 10.65 |

TABLE 2

Second study in mice (45 days): Liver enzyme
levels and electrolyte composition
Fairly consistent across the group

|  | ALB g/dL | ALP U/L | ALT U/L | AMY U/L | TBIL mg/dL | BUN mg/dL | TP g/dL | GLOB g/dL | CRE mg/dL |
| --- | --- | --- | --- | --- | --- | --- | --- | --- | --- |
| Mouse 1 | 2.6 | 7 | 145 | 0 | 0.3 | 18 | 3.7 | 1.1 | 0 |
| Mouse 2 | 2.2 | 17 | 202 | 497 | 0.3 | 10 | 3.5 | 1.3 | 0 |
| Mouse 3 | 2.8 | 35 | 52 | 617 | 0.3 | 15 | 4.3 | 1.6 | 0 |
| Mouse 4 | 2.8 | 15 | 50 | 637 | 0.2 | 14 | 4.1 | 1.2 | 0 |
| Mouse 5 | 2.5 | 24 | 126 | 602 | 0.3 | 11 | 4.1 | 1.6 | 0 |
| Average | 2.58 | 19.60 | 115.00 | 470.60 | 0.28 | 13.60 | 3.94 | 1.36 | 0.00 |
| Stdev | 0.25 | 10.53 | 64.78 | 268.58 | 0.04 | 3.21 | 0.33 | 0.23 | 0.00 |

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention claimed is:

1. A composite hydrogel comprising
   at least one non-peptidic polymer and
   at least one peptide,
wherein said peptide is selected from the group consisting of Z-LIVAGDD-Z'$_p$ (SEQ ID NO: 1), Z-LIVAGDE-Z'$_p$(SEQ ID NO: 2), Z-LIVAGED-Z'$_p$(SEQ ID NO: 3), Z-LIVAGEE-Z'$_p$(SEQ ID NO: 4), Z-LIVAGKC-Z'$_p$(SEQ ID NO: 5), Z-LIVAGSC-Z'$_p$(SEQ ID NO: 6), Z-AIVAGKC-Z'$_p$(SEQ ID NO: 7), Z-AIVAGSC-Z'$_p$(SEQ ID NO: 8), Z-LIVAGC-Z'$_p$ (SEQ ID NO: 9), Z-LIVAGD-Z'$_p$(SEQ ID NO: 10), Z-AIVAGD-Z'$_p$(SEQ ID NO: 14), Z-LIVAGE-Z'$_p$(SEQ ID NO: 15), Z-LIVAGK-Z'$_p$(SEQ ID NO: 16), Z-LIVAGS-Z'$_p$ (SEQ ID NO: 17), Z-ILVAGS-Z '$_p$(SEQ ID NO: 18), Z-AIVAGS-Z'$_p$(SEQ ID NO: 19), Z-LIVAGT-Z'$_p$(SEQ ID NO: 20), Z-AIVAGT-Z'$_p$(SEQ ID NO: 21), Z-ILVAGK-Z'$_p$ (SEQ ID NO: 49), Z-ILVAG(Orn)-Z'$_p$(SEQ ID NO: 50), Z-ILVAG(Dab)-Z'$_p$(SEQ ID NO: 51), Z-ILVAG(Dap)-Z'$_p$ (SEQ ID NO: 52), Z-ILVAGS-Z'$_p$(SEQ ID NO: 53), Z-AIVAGK-Z'$_p$(SEQ ID NO: 55), Z-AIVAG(Orn)-Z '$_p$(SEQ ID NO: 56), Z-AIVAG(Dab)-Z '$_p$(SEQ ID NO: 57), Z-AIVAG(Dap)-Z'$_p$(SEQ ID NO: 58), Z-LIVAG(Orn)-Z'$_p$ (SEQ ID NO: 59), Z-LIVAG(Dab)-Z'$_p$(SEQ ID NO: 60), and Z-LIVAG(Dap)-Z'$_p$(SEQ ID NO: 61;
wherein
   Z is an N-terminal protecting group wherein said N-terminal protecting group has the general formula —C(O)—R, wherein R is selected from the group consisting of H, and alkyl;
   Z' is a C-terminal protecting group wherein said C-terminal protecting group is an amide group or an ester group;
   p is selected from 0 or 1;
wherein when the non-peptidic polymer is a cationic polymer comprising chitosan or poly (amido amine) dendrimers a polar amino acid or a polar amino acid derivative of the peptide adjacent to Z' consists of an acidic polar amino acid or an acidic polar amino acid derivative; wherein when the non-peptidic polymer is a neutral polymer comprising polyethylene glycol (PEG), then the polar amino acid or polar amino acid derivative of the peptide adjacent to Z' consists of a neutral polar amino acid, a neutral polar amino acid derivative, a basic polar amino acid or a basic polar amino acid derivative; and wherein when the non-peptidic polymer is an anionic polymer comprising a nucleic acids, chondroitin sulphate or hyaluronic acid, then the polar amino acid or polar amino acid derivative of the peptide adjacent to Z' consists of a basic polar amino acid or a basic polar amino acid derivative.

2. The composite hydrogel of claim 1, wherein the hydrophobicity decreases from the N-terminus to the C-terminus of said peptide.

3. The composite hydrogel of any of claim 1, wherein said acidic polar amino acid and acidic polar amino acid derivative are selected from the group consisting of aspartic acid (Asp, D), glutamic acid (Glu, E), and cysteine (Cys, C), and wherein said basic polar amino acid and basic polar amino acid derivative are selected from the group consisting of serine (Ser, S), threonine (Thr, T), allo-threonine, lysine (Lys, K), ornithine (Orn), 2,4-diaminobutyric acid (Dab), and 2,4-diaminopropionic acid (Dap.

4. The composite hydrogel of claim 1, wherein said acidic polar amino acid and acidic polar amino acid derivative are selected from aspartic acid (Asp, D) and glutamic acid (Glu, E), or wherein said basic polar amino acid and basic polar amino acid derivative are selected from the group consisting of lysine (Lys, K), ornithine (Orn), 2,4-diaminobutyric acid (Dab), and 2,4-diaminopropionic acid (Dap).

5. The composite hydrogel of claim 1, wherein said cationic polymer is a hydrophilic or amphiphilic polymer, and said non-peptidic polymer is a linear or branched polymer, wherein said branched polymer is a dendrimer.

6. The composite hydrogel of claim 1, wherein said cationic polymer is selected from the group consisting of chitosan, and poly(amido amine) dendrimers,
   said anionic polymer is selected from the group consisting of nucleic acids, comprising RNA and DNA, said neutral polymer is polyethylene glycol (PEG), wherein said PEG is selected from diethylene glycol diacrylate (DEGDA), bi-functional PEG, N-hydroxysuccinimide-PEG-maleimide and bis(succinimidyl) polyethylene glycol (BS-PEG).

7. The composite hydrogel of claim 1, wherein the composite hydrogel further comprises at least one bioactive agent, wherein said at least one bioactive agent is selected from the group consisting of nucleic acids, (poly)peptides, virus particles, oligosaccharides, polysaccharides, vitamins, sialic acids, antigens, antibiotics, anti-inflammatory molecules, vaccines, drugs, prodrugs, nanoparticles and other organic or inorganic compounds.

8. The composite hydrogel of claim 7, wherein said at least one bioactive agent is selected from a growth factor or cell adhesion molecule, a nucleic acid encoding a growth factor and a cell adhesion molecule, wherein said growth factor comprises a cytokine, and said nucleic acid encodes a cytokine.

9. The composite hydrogel of claim 7, wherein said at least one bioactive agent is encapsulated by said composite hydrogel, or wherein said at least one bioactive agent is conjugated to said composite hydrogel, wherein said at least one bioactive agent is coupled to at least one functional group present on said non-peptidic polymer or to at least one functional group present on said peptide, wherein said at least one functional group is selected from the group consisting of amines, carboxylic acids, thiols, alcohols, carbohydrates, amides, imines, imides, azides, nitriles, peroxides, esters, thioesters, phosphates, aryls, aldehydes, ketones, sulfates, sulfites, nitrates, nitrites, phosphonates, silanes, alkanes, alkenes and alkynes.

10. The composite hydrogel of claim 7, wherein said at least one bioactive agent is a negatively charged bioactive agent, and said non-peptidic polymer is a cationic polymer, or wherein said at least one bioactive agent is a positively charged bioactive agent, and said non-peptidic polymer is an anionic polymer, or wherein said at least one bioactive agent is a neutral bioactive agent, and said non-peptidic polymer is a neutral polymer.

11. The composite hydrogel of claim 1, wherein said nucleic acid comprises an oligonucleotide, polynucleotide, DNA, RNA, modified and artificial nucleic acids and nucleic acid analogues, or combinations thereof, wherein said nucleic acid is selected from the group consisting of oligonucleotide, polynucleotide, plasmid DNA, aptamers, mRNA, microRNA, siRNA and short hairpin RNA.

12. The composite hydrogel of claim 11, wherein said nucleic acid is a bioactive agent or encodes a bioactive agent, a growth factor, or a cell adhesion molecule, and/or wherein said nucleic acid is conjugated to a bioactive agent.

13. The composite hydrogel of claim 1, wherein said at least one non-peptidic polymer is present at a concentration of 50% (w/w) or less, with respect to the total weight of said composite hydrogel, or wherein said at least one non-peptidic polymer is present at a concentration of 40% (w/w) or less, with respect to the total weight of said composite hydrogel, or wherein the total nucleic acid content of said composite hydrogel is 50% or less by charge ratio.

14. A pharmaceutical or cosmetic composition comprising a composite hydrogel of claim 1.

15. A method of producing a composite hydrogel of claim 1, comprising the steps of:
preparing an aqueous solution of a mixture of said at least one non-peptidic polymer of claim 1 and said at least one peptide of claim 1; or
treating a preformed hydrogel comprising said at least one peptide with a solution of said at least one non-peptidic polymer, optionally further comprising at least one of the steps of:
adding at least one bioactive agent;
adding an ultraviolet (UV) photoinitiator to said aqueous solution and exposing said aqueous solution to UV irradiation;
adding at least one coupling reagent to facilitate the formation of covalent linkages;
adding at least one compound acting as gelation enhancer;
adding at least one buffer, preferably at least one physiologically acceptable buffer.

16. A method comprising culturing cells with a 3-D scaffold of the composite hydrogel of claim 1, wherein the scaffold allows for the embedding of the cells.

17. The method of claim 16, wherein said cells are stem cells, including embryonic stem cells, human induced pluripotent stem cells (iPS), progenitor cells, adult stem cells, cord blood stem cells, mesenchymal stem cells, adipose-derived stem cells, and hematopoietic stem cells.

18. A method for delivery of a drug or a bioactive agent to a subject, comprising administering to the subject the composite hydrogel of claim 1 that comprises the drug or bioactive agent.

19. The method of claim 18, wherein the delivery is for sustained or controlled release, or as an implant or as an injectable agent that gels in situ.

20. A 3-D scaffold for culturing cells comprising a composite hydrogel of claim 1, wherein said cells are preferably stem cells, including embryonic stem cells, human induced pluripotent stem (iPS) cells, progenitor cells and adult stem cells, cord blood stem cells, mesenchymal stem cells, adipose-derived stem cells, hematopoietic stem cells.

21. An implant or injectable agent comprising a composite hydrogel of claim 1.

* * * * *

UNITED STATES PATENT AND TRADEMARK OFFICE
CERTIFICATE OF CORRECTION

PATENT NO. : 10,449,257 B2
APPLICATION NO. : 14/356116
DATED : October 22, 2019
INVENTOR(S) : Charlotte Hauser et al.

It is certified that error appears in the above-identified patent and that said Letters Patent is hereby corrected as shown below:

In the Claims

Column 65, Line 53, Claim 1, please amend as follows:
1. A composite hydrogel comprising
 at least one non-peptidic polymer and
 at least one peptide,
wherein said peptide is selected from the group consisting of Z-LIVAGDD-Z'p (SEQ ID NO: 1), Z-LIVAGDE-Z'p (SEQ ID NO: 2), Z-LIVAGED-Z'p (SEQ ID NO: 3), Z-LIVAGEE-Z'p (SEQ ID NO: 4), Z-LIVAGKC-Z'p (SEQ ID NO: 5), Z-LIVAGSC-Z'p (SEQ ID NO: 6), Z-AIVAGKC-Z'p (SEQ ID NO: 7), Z-AIVAGSC-Z'p (SEQ ID NO: 8), Z-LIVAGC-Z'p (SEQ ID NO: 9), Z-LIVAGD-Z'p (SEQ ID NO: 10), Z-AIVAGD-Z'p (SEQ ID NO: 14), Z-LIVAGE-Z'p (SEQ ID NO: 15), Z-LIVAGK-Z'p (SEQ ID NO: 16), Z-LIVAGS-Z'p (SEQ ID NO: 17), Z-ILVAGS-Z'p (SEQ ID NO: 18), Z-AIVAGS-Z'p (SEQ ID NO: 19), Z-LIVAGT-Z'p (SEQ ID NO: 20), Z-AIVAGT-Z'p (SEQ ID NO: 21), Z-ILVAGK-Z'p (SEQ ID NO: 49), Z-ILVAG(Orn)-Z'p (SEQ ID NO: 50), Z-ILVAG(Dab)-Z'p (SEQ ID NO: 51), Z-ILVAG(Dap)-Z'p (SEQ ID NO: 52), Z-ILVAGS-Z'p (SEQ ID NO: 53), Z-AIVAGK-Z'p (SEQ ID NO: 55), Z-AIVAG(Orn)-Z'p (SEQ ID NO: 56), Z-AIVAG(Dab)-Z'p (SEQ ID NO: 57), Z-AIVAG(Dap)-Z'p (SEQ ID NO: 58), Z-LIVAG(Orn)-Z'p (SEQ ID NO: 59), Z-LIVAG(Dab)-Z'p (SEQ ID NO: 60), and Z-LIVAG(Dap)-Z'p (SEQ ID NO: 61,
wherein
 Z is an N-terminal protecting group wherein said N-terminal protecting group has the general formula –C(O)–R, wherein R is selected from the group consisting of H, and alkyl;
 Z' is a C-terminal protecting group wherein said C-terminal protecting group is an amide group or an ester group;
 p is selected from 0 or 1;
wherein when the non-peptidic polymer is a cationic polymer comprising chitosan or poly (amido amine) dendrimers a polar amino acid or a polar amino acid derivative of the peptide adjacent to Z' consists of an acidic polar amino acid or an acidic polar amino acid derivative; wherein when the non-peptidic polymer is a neutral polymer comprising polyethylene glycol (PEG), then the polar amino acid or polar amino acid derivative of the peptide adjacent to Z' consists of a neutral polar amino acid, a neutral polar amino acid derivative, a basic polar amino acid or a basic polar amino Signed and Sealed this
Nineteenth Day of May, 2020

Andrei Iancu
*Director of the United States Patent and Trademark Office* acid derivative; and wherein when the non-peptidic polymer is an anionic polymer comprising a nucleic acid, chondroitin sulphate or hyaluronic acid, then the polar amino acid or polar amino acid derivative of the peptide adjacent to Z' consists of a basic polar amino acid or a basic polar amino acid derivative.

Column 66, Line 9, Claim 3, please amend as follows:
3. The composite hydrogel of any of claim 1, wherein said acidic polar amino acid and acidic polar amino acid derivative are selected from the group consisting of aspartic acid (Asp, D), glutamic acid (Glu, E), and cysteine (Cys, C), and wherein said basic polar amino acid and basic polar amino acid derivative are selected from the group consisting of serine (Ser, S), threonine (Thr, T), allo-threonine, lysine (Lys, K), ornithine (Orn), 2,4-diaminobutyric acid (Dab), and 2,4-diaminopropionic acid (Dap).

Column 67, Line 4, Claim 11, please amend as follows:
11. The composite hydrogel of claim 1, wherein said nucleic acid comprises an oligonucleotide, polynucleotide, DNA, RNA, modified and artificial nucleic acids and nucleic acid analogues, or combinations thereof, or wherein said nucleic acid is selected from the group consisting of oligonucleotide, polynucleotide, plasmid DNA, aptamers, mRNA, microRNA, siRNA and short hairpin RNA.